(12) United States Patent
Wang et al.

(10) Patent No.: US 7,956,997 B2
(45) Date of Patent: Jun. 7, 2011

(54) SYSTEMS AND METHODS FOR FOOD SAFETY DETECTION

(75) Inventors: Hong Wang, Cupertino, CA (US); Xun Guo, Sacramento, CA (US); Chunwei Liu, Beijing (CN)

(73) Assignee: OptoTrace Technologies, Inc., Mountain View, CA (US)

( * ) Notice: Subject to any disclaimer, the term of this patent is extended or adjusted under 35 U.S.C. 154(b) by 387 days.

(21) Appl. No.: 12/246,616

(22) Filed: Oct. 7, 2008

(65) Prior Publication Data

US 2009/0046284 A1 Feb. 19, 2009

Related U.S. Application Data

(63) Continuation-in-part of application No. 12/176,383, filed on Jul. 20, 2008, which is a continuation-in-part of application No. 11/681,157, filed on Mar. 1, 2007, now Pat. No. 7,428,046, which is a continuation of application No. 10/987,842, filed on Nov. 12, 2004, now Pat. No. 7,242,469, which is a continuation-in-part of application No. 10/852,787, filed on May 24, 2004, now Pat. No. 7,384,792.

(60) Provisional application No. 60/473,283, filed on May 27, 2003, provisional application No. 60/473,287, filed on May 27, 2003, provisional application No. 60/520,222, filed on Nov. 17, 2003.

(51) Int. Cl.
*G01J 3/44* (2006.01)
(52) U.S. Cl. ...................................................... 356/301
(58) Field of Classification Search .................... 356/301
See application file for complete search history.

(56) References Cited

U.S. PATENT DOCUMENTS

| | | | |
|---|---|---|---|
| 4,933,274 A | 6/1990 | Sanford | |
| 5,017,007 A | 5/1991 | Milne | |
| 5,244,788 A | 9/1993 | Hubscher | |
| 5,527,712 A | 6/1996 | Sheehy | |
| 5,796,476 A * | 8/1998 | Wang et al. | 356/301 |
| 5,864,397 A | 1/1999 | Vo-Dinh | |
| 6,361,861 B2 | 3/2002 | Gao | |
| 6,406,777 B1 | 6/2002 | Boss | |
| 6,614,523 B1 | 9/2003 | Boss | |
| 2002/0123050 A1 | 9/2002 | Poponin | |
| 2003/0059820 A1 | 3/2003 | Vo-Dinh | |
| 2003/0175472 A1 | 9/2003 | Den | |
| 2004/0106203 A1 | 6/2004 | Stasiak | |
| 2005/0136552 A1 | 6/2005 | Buechler | |
| 2005/0196876 A1 * | 9/2005 | Chan et al. | 436/518 |
| 2006/0055922 A1 * | 3/2006 | Li et al. | 356/301 |
| 2008/0096005 A1 * | 4/2008 | Premasiri | 356/301 |

* cited by examiner

*Primary Examiner* — Kara E Geisel
(74) *Attorney, Agent, or Firm* — SV Patent Service

(57) ABSTRACT

A method for detecting an ingredient in a food product includes establishing a spectral signature in a Raman spectrum obtained from a chemical substance; allowing a food sample solution obtained from a food product to come to contact with a first nano-scale surface structure in a first sensor, wherein the first sensor comprises a substrate, wherein the nano-scale surface structure comprises a plurality of columns over the substrate or a plurality of holes in the substrate; illuminating the food sample solution and the first nano-scale surface structure on the first sensor by a laser beam; scattering the laser beam by the food sample solution and the first nano-scale surface structure to produce a scattered light; obtaining a first Raman spectrum from the scattered light using a spectral analyzer; and identifying the spectral signature in the first Raman spectrum to determine the existence of the chemical substance in the food product.

30 Claims, 27 Drawing Sheets

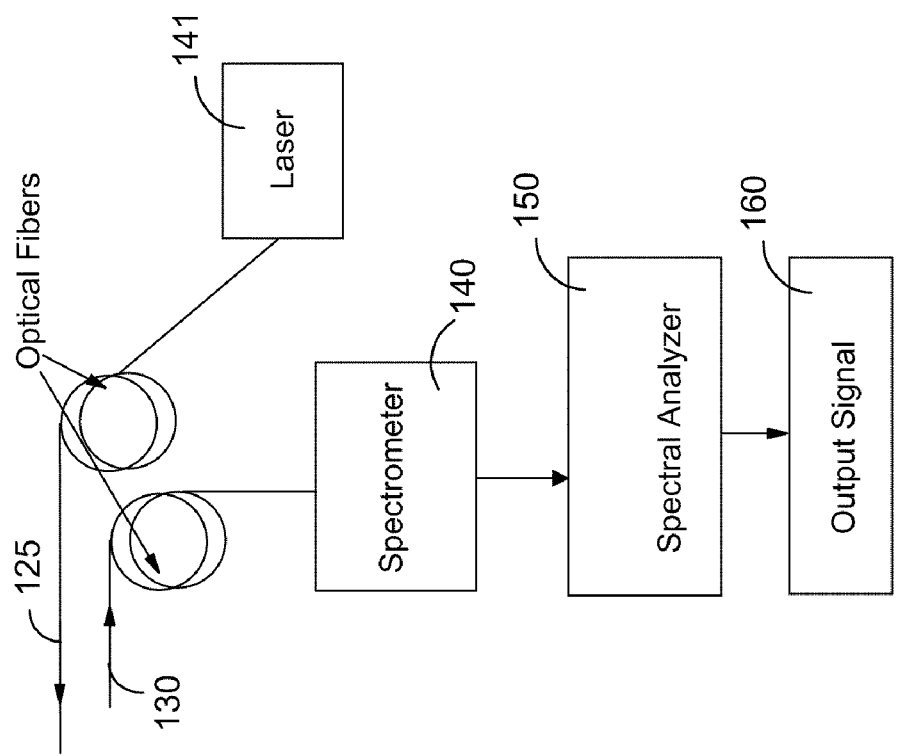
Fig. 1C
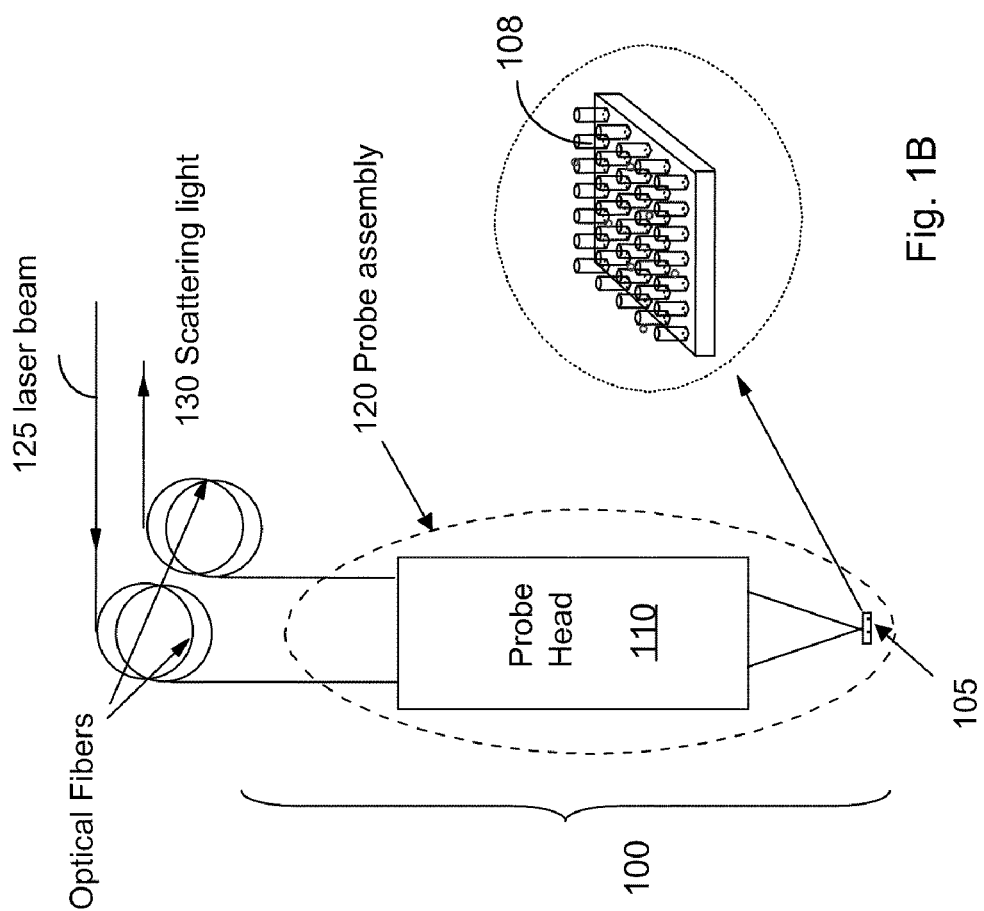
Fig. 1B
Fig. 1A

SECTION A-A

SYSTEMS AND METHODS FOR FOOD SAFETY DETECTION

The present application is a Continuation-in-Part (CIP) patent application of commonly assigned pending U.S. patent application Ser. No. 12/176,383, entitled "Non-invasive disease diagnosis using light scattering probe", filed Jul. 20, 2008. U.S. patent application Ser. No. 12/176,383 is a CIP of commonly assigned U.S. patent application Ser. No. 11/681,157 (now issued as U.S. Pat. No. 7,428,046), entitled "Trace chemical optical probe", filed Mar. 1, 2007. U.S. patent application Ser. No. 11/681,157 is a continuation application of commonly assigned U.S. patent application Ser. No. 10/987,842 filed Nov. 12, 2004 (now issued as U.S. Pat. No. 7,242,469), which is a CIP patent application of U.S. patent application Ser. No. 10/852,787 (now issued as U.S. Pat. No. 7,384,792) filed on May 24, 2004. U.S. patent application Ser. No. 10/852,787 claims priority to Provisional Patent Applications 60/473,283 and 60/473,287 filed on May 27, 2003, and Provisional Patent Application 60/520,222 filed on Nov. 17, 2003. There disclosure of these related patent applications are incorporated herein by reference.

BACKGROUND

This invention relates generally to the methods and systems for detection of very small amount of chemicals (trace chemicals) by employing light scattering probes. More particularly, this invention relates to an improved light scattering probe and a chemical sensor.

Despite the fact Raman detectors have sensitivity down to a level of single molecule detection (SMD), due to several technical difficulties; conventional Raman sensors still have very limited applications. Specifically, one of the major limitations of Raman spectroscopy application is the weak Raman scattering signal for trace chemical detection. There have been many efforts to attempt to resolve the problem of low scattering signals in the field of Raman sensing. However, such efforts still have very limited success and have not been able to make Raman detectors available for practical and economical applications that urgently require ultra sensitive chemical trace detections.

Therefore, a need still exists in the art to provide practical configuration for conveniently implement the Raman sensors in applications to antiterrorism, forensic, medical diagnoses, disease preventions, industrial process monitoring, environmental cleaning up and monitoring, food detection for food safety, and drug quality control, etc.

SUMMARY OF THE INVENTION

In one aspect, the present invention relates to a method for detecting an ingredient in a food product. The method includes establishing a spectral signature in a Raman spectrum obtained from a chemical substance; allowing a food sample solution obtained from a food product to come to contact with a first nano-scale surface structure in a first sensor, wherein the first sensor comprises a substrate, wherein the nano-scale surface structure comprises a plurality of columns over the substrate or a plurality of holes in the substrate; illuminating the food sample solution and the first nano-scale surface structure on the first sensor by a laser beam; scattering the laser beam by the food sample solution and the first nano-scale surface structure to produce a scattered light; obtaining a first Raman spectrum from the scattered light using a spectral analyzer; and identifying the spectral signature in the first Raman spectrum to determine the existence of the chemical substance in the food product.

In another aspect, the present invention relates to a method for detecting an ingredient in a food product. The method includes allowing a reference sample solution containing the chemical substance to come to contact with a first nano-scale surface structure in a first sensor; obtaining a first Raman spectrum from the reference solution and the nano surface to establish a spectral signature in the first Raman spectrum for the chemical substance; allowing a food sample solution obtained from a food product to come to contact with a second nano-scale surface structure in a second sensor; illuminating the food sample solution and the second nano-scale surface structure on the second sensor by a laser beam; scattering the laser beam by the food sample solution and the second nano-scale surface structure to produce a scattered light; obtaining a second Raman spectrum from the scattered light using a spectral analyzer; and identifying the spectral signature in the second Raman spectrum to determine the existence of the chemical substance in the food product.

In another aspect, the present invention relates to a method for detecting an ingredient in a food product. The method includes allowing a reference sample solution containing the chemical substance to come to contact with a first nano-scale surface structure in a first sensor, wherein the first nano-scale surface structure includes a plurality of nano particles on a surface of the first sensor, or a plurality of columns or holes having an average neighboring distance in a range from 10 nanometers to 1000 nanometers; obtaining a first Raman spectrum from the reference solution and the nano surface to establish a spectral signature around a predetermined wavelength in the first Raman spectrum for the chemical substance, wherein the spectral signature includes at least one spectral peak around the predetermined wavelength in the first Raman spectrum; allowing a food sample solution obtained from a food product to come to contact with a second nano-scale surface structure in a second sensor, wherein the first sensor and the second sensor have substantially the same nano surface structures; illuminating the food sample solution and the second nano-scale surface structure on the second sensor by a laser beam; scattering the laser beam by the food sample solution and the second nano-scale surface structure to produce a scattered light; obtaining a second Raman spectrum from the scattered light using a spectral analyzer; identifying the spectral signature around the predetermined wavelength in the second Raman spectrum to determine the existence of the chemical substance in the food product, wherein the step of identifying comprises determining if the spectral peak in the Raman spectrum or a signal-to-noise ratio for the spectral peak is above a pre-determined threshold value; and positively identifying the chemical substance if the spectral peak or the signal-to-noise ratio is above the pre-determined threshold value.

Implementations of the system may include one or more of the following. The step of establishing can include allowing a reference sample solution containing the chemical substance to come to contact with a second nano-scale surface structure in a second sensor; and obtaining a second Raman spectrum from the reference solution and the nano surface to establish the spectral signature in the Raman spectrum for the chemical substance. The first sensor and the second sensor can have substantially the same nano surface structures. The sensor can further include a conductive material on the substrate. The method can further include: during the step of illuminating, applying an electric potential to the conductive material in the first nano-scale surface structure to enhance charge transfer between molecules of the conductive material and the conductive material in the first nano-scale surface structure. The conductive layer can include a noble metal. The sensor can include a plurality of holes at least partially in the conductive material. The plurality of columns can be formed on the conductive material. The step of identifying can include identifying a spectral signature around a predetermined wavelength in the first Raman spectrum. The spectral signature can include at least one spectral peak around the predetermined wavelength in the first Raman spectrum. The step of identifying can include determining if the spectral peak in the Raman spectrum or a signal-to-noise ratio for the spectral peak is above a pre-determined threshold value; and positively identifying the chemical substance if the spectral peak or the signal-to-noise ratio is above the pre-determined threshold value. The method can further include determining a concentration of the chemical substance using the spectral signature if the chemical substance is determined to exist in the food product. The food product can include dairy products, candies, drinks, alcohol, meat, seafood, tea, fresh or canned vegetables, fruits, grain products, cereals, corn chips, potato chips, or protein containing food. The dairy products can include milk, milk powders, cheese, cheese-containing cakes, yoghurts, ice creams, or milk containing candies. The chemical substance can include melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, or enorfloxacin. The chemical substance can include a pesticide, an insecticide, or an antibiotic. The product can include a dairy product, wherein the chemical substance includes melamine, wherein the spectral signature comprises one or more of spectral peaks at about 678 $cm^{-1}$, 698 $cm^{-1}$, or 712 $cm^{-1}$, or at about 1648 $cm^{-1}$. The method can further include adding acetonitrile to the food sample solution, wherein the spectral signature can include one or more of spectral peaks at about 918 $cm^{-1}$-921 $cm^{-1}$. The chemical substance can include protein, wherein the spectral signature can include one or more of spectral peaks at about 1658 $cm^{-1}$. The chemical substance can include starch, wherein the spectral signature can include one or more of spectral peaks at about 473 $cm^{-1}$. The first nano-scale surface structure in a first sensor can include a plurality of columns or a plurality of holes having an average neighboring distance in a range from 10 nanometers to 1000 nanometers. The method can further include introducing nano particles on a surface of the first sensor, wherein the first nano-scale surface structure includes the nano particles on the surface of the first sensor. The method can further include suspending the nano particles in the food sample solution; and introducing the food sample solution to the surface of the first sensor.

Embodiments may include one or more of the following advantages. The disclosed systems and methods provide simple and non-invasive approach to detect a disease in a patient. The disclosed systems are portable and easy to operate, and are thus ideal for being used for early disease prevention, and in-field drug usage screening. The disclosed systems and methods are suitable for early detect and diagnosis. The disclosed systems and methods also have short testing cycle, and can therefore be very helpful for monitoring progresses in the treatment of diseases and drug use. The disclosed systems and methods can detect a wide range of disease such as oral cancer, breast cancer, lung cancer, stomach cancer, liver cirrhosis, a failing kidney, ulcer cancer, ovarian cancer, uterus cancer, cervical cancer, oral cancer, esophageal cancer, thyroid cancer, larynx cancer, leukemia, colon cancer, bladder cancer, prostate cancer, bronchus cancer, pancreas cancer, diabetes, HIV, smoking status as well as illicit drug use.

The present application describes applications of Raman scattering probe with or without a sensor. Since a sensor provides much higher sensitivity in SERS compared with conventional enhance surface, some applications that were not practical before have now become practically achievable. Because the significant improvement in Raman scattering achieved by the sensor broader scopes of applications are now enabled and can be practically implemented as now disclosed in this application.

The disclosed light sensing systems and methods do not require high detection sensitivities can thus be used in a wide range of applications. Such applications include, but not limited, homeland security to detect trace chemicals of explosives, biochemical weapons and illegal drug smuggling; food and drinking materials safety to detect pesticide residues; early disease diagnosis; environmental monitoring; industrial process monitoring, and so on.

In one aspect, the trace chemicals to be detected can be in the form of a gas, a liquid, and a solid. The molecules are adsorbed onto the surface of the sensor. The adsorbed molecules have much larger scattering cross section than that they are free form in gas, liquid or solid. When laser beam illuminates the adsorbed molecules, Raman Scattering spectrum of the molecules can be obtained. Target chemicals can be identified since most molecules have their unique Raman spectral signatures.

In another aspect, the laser beam is directed to illuminate a sensor coated a sample solution containing suspended nano particles. The scattering light is collected from sample directly. The disclosed technologies are applicable to detecting harmful and authorized ingredients in food products and to determining concentrations of useful ingredients in food products. The disclosed methods and systems are also applicable to disease diagnosis, product (e.g. jewelry) authentication for patent and copyright protection.

BRIEF DESCRIPTION OF THE DRAWINGS

The following drawings, which are incorporated in and from a part of the specification, illustrate embodiments of the present invention and, together with the description, serve to explain the principles of the invention.

FIGS. 1A-1C illustrate exemplified configurations of trace chemical detection using Surface-Enhance Raman Scattering.

DETAILED DESCRIPTION OF THE EMBODIMENT

Figure 2:
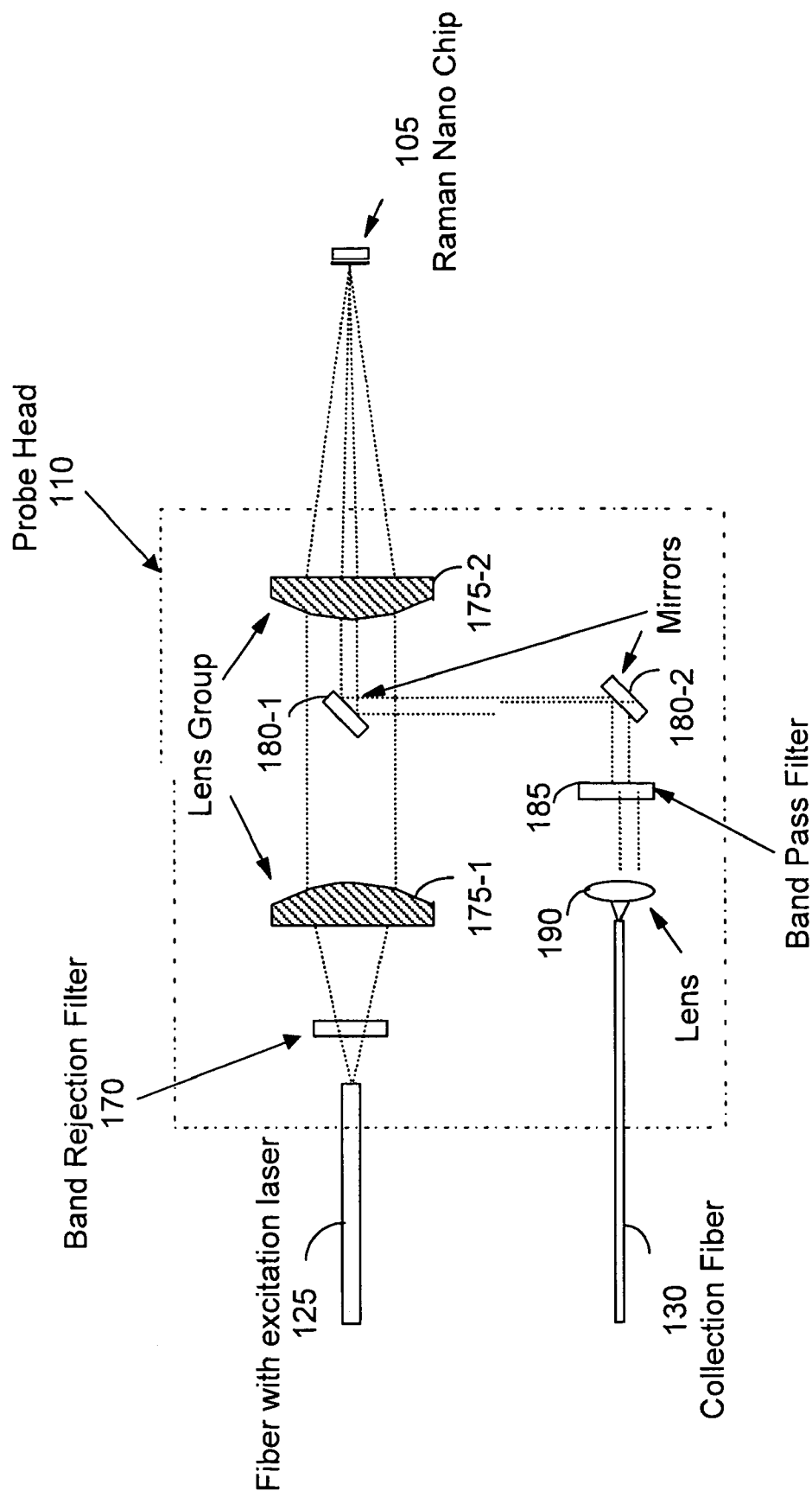
FIG. 2 illustrates an exemplified design of a probe head for Raman scattering probe.

Referring to FIG. 1A, a light scattering probe 100 includes a probe head 110 and a sensor 105. The sensor 105 includes a nano surface structure. The nano surface structure can include a plurality of nano rods 108, as shown in FIG. 1B, a plurality of nano holes, or other surface structures having dimensions at nanometer scale. In some embodiments, as described below, nano surface structures can be prepared by coating the surface of the sensor 105 of a solution containing a colloidal suspension of nano particles. The solution can be subsequently evaporated to deposit the nano particles on the surface.

Using the example of nano surface comprising nano rods 108, a sample fluid can be introduced to the nano rods 108 in the sensor 105. The sample fluid can include a body fluid obtained from a patient or an illicit drug user for disease diagnosis and drug use determination. Examples of the body fluid can include blood, saliva, urine, serum, tear, sweat, and stomach fluid. The sample can also include a food sample for detecting harmful or illegal additives in a food product to ensure food safety. Examples of good products include dairy products such as milk, milk powder (e.g., baby formula), cheese, yoghurt, ice cream, milk containing candies, other milk contained food products, and protein-containing food products. The probe head 110 and the sensor 105 are enclosed in a probe assembly 120. The probe assembly 120 can be depressurized by a vacuum pump to reduce contamination of the sensing surfaces for foreign substance.

A laser beam emitted by a laser 141 is guided by optical fibers 125 to illuminate the sensor 105, as shown in FIG. 1C. The probe head 110 is positioned adjacent to the sensor 105. In the present application, the term RamanNanoChip™ refers to a sensor comprising a nano-scale surface structure that is configured to adsorb molecules of a chemical, biological, or medical sample for detecting using a light scattering probe. The scattered light is collected by the probe head 110 and guided to a spectral analyzer 150 along by an optical fiber 130. A Raman spectrum of the scattered light is obtained by the spectral analyzer 150. The spectral signatures in the Raman spectrum are identified and to compared with database of spectral signatures for various molecules. An output signal can indicate identification of a disease when a threshold of certain molecules under detection is exceeded. In the present specification, the term "spectral signature" can refer to one or more spectral peaks, one or more spectral valleys, and other spectral shapes such as relative peak height, peak line width, peak shape, etc., that characterize one of more molecular bonds in a biological, medical, or chemical materials.

Referring to FIG. 2, the probe head 110 can receive a laser projection from an input laser fiber 125 to pass through a band ejection filter 170 to pass through a lens group 175-1 and 175-2 to project onto sensor 105. A scattering light is projected back to a group of mirrors 180-1 and 180-2 to pass through another band-pass filter 185 and a collimated lens to output from the collection fiber 130.

Figure 3A:
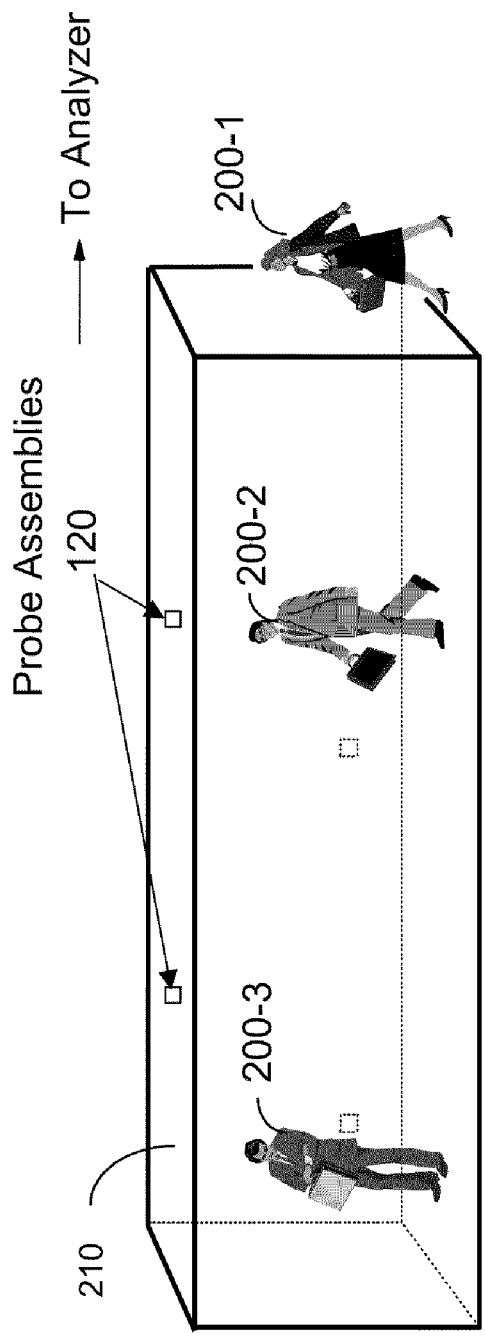
FIGS. 3A and 3B are schematic diagrams respectively showing inspections of passengers and luggage using a Raman scattering probe at an airport.

FIG. 3A is a schematic diagram to show a configuration of the Surface Enhance Raman Scattering application in safety of transportation and other places where a passenger screening is required to monitor passengers 200-1, 200-2, and 200-3. For passenger screening, the probe assembly 120 with embedded sensor 105 is placed in the passageway 210. The probes head 120 are connected by fibers to the spectral analyzer 150 in office near or far away from it. The probe head 120 is aligned to point to the sensing surface of a sensor 105 and they are packaged together. The passageway tunnel 210 can be forced ventilated and under little negative pressure and/or little higher temperature to increase evaporation of harmful materials. If a passenger, e.g., passenger 200-2, carrying explosive materials, harmful chemicals, chemical weapons, bio-chemical weapons, nuclear weapons or narcotic drugs, few molecules of such materials will volatilize into air that molecules are adsorbed onto the surface of a sensor through specially designed sample collection system. The Raman Spectrum will be recorded and compared with database in mainframe at office. As soon as the harmful materials are detected, early stage alarm signal will be triggered and appropriate security actions can be further processed.

Figure 3B:
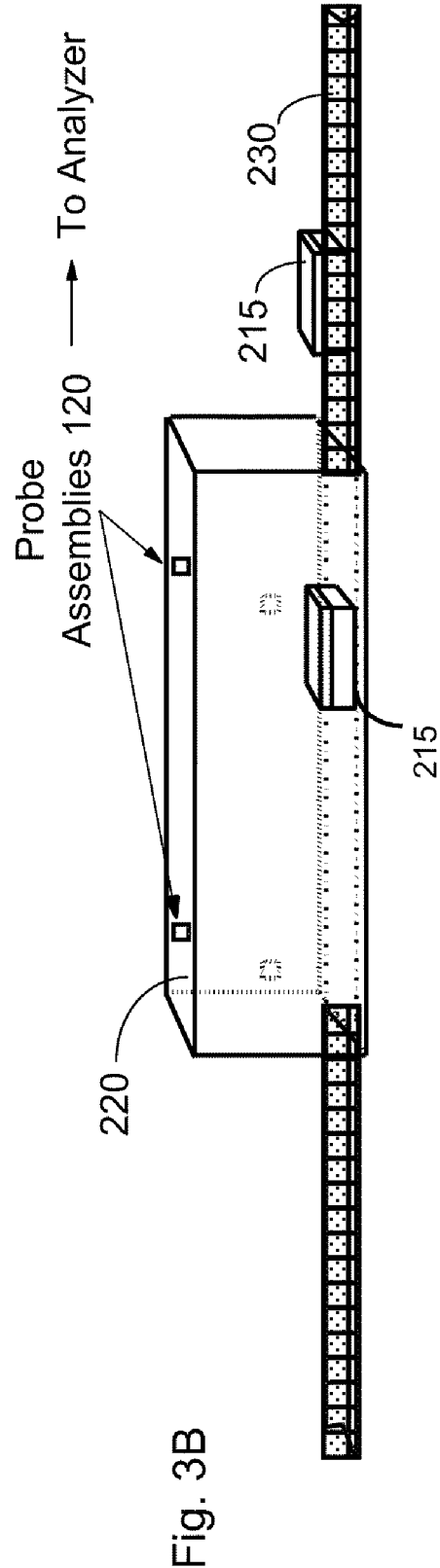

FIG. 3B is a diagram to show application implemented to monitor luggage 215 for freight transportation carried by a conveyer 230 to pass through cargo screening channel 220. The probe assembly 120 with embedded sensor 105 is placed around the cargo screen channel 220. The probes head 120 are connected with fibers to the spectral analyzer 150 in office near or far away from it. The probe head 120 is aligned to the surface of a sensor 105 and they are packaged together to detect any explosives, chemical or biochemical weapon, or harmful chemicals enclosed in the luggage 215. This configuration can be implemented in other applications such as mail stations, railway stations, custom inspection areas, traffic control zones, etc. This configuration can be easily implemented to detect gun powders or other explosives or hazardous materials.

Figure 4:
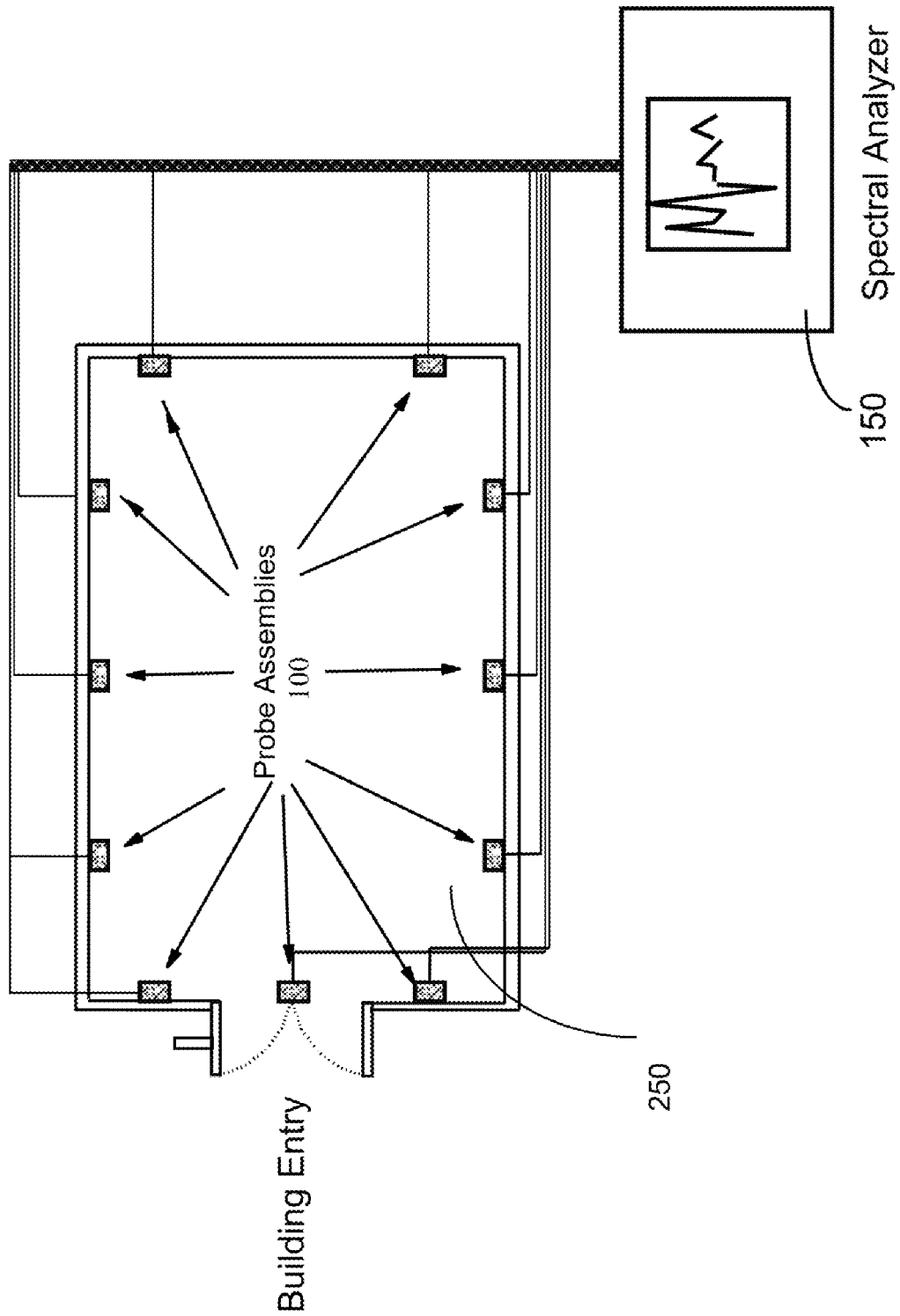
FIG. 4 is a schematic diagram showing safety monitoring in public building safety using a Raman scattering probe.

FIG. 4 is schematic diagram of Surface-Enhance Raman Scattering applications using a sensor in safety of public buildings 250 such as airport, railway or bus stations, ballpark buildings, Federal buildings, auditoriums, theaters, courthouses, and other public buildings. The light scattering probe 100 that includes probe head 120 combined with a sensor 10 are distributed in the public buildings or others protected areas. The light scattering probes 100 are applied to monitor many different molecular substances to provide earlier detection of any dangerous or harmful chemicals enter into the monitor areas. Particular examples of hazardous material monitoring include, but not limited to detection of explosive materials, chemical or biochemical weapons including anthrax, drugs, and so on.

Figure 5:
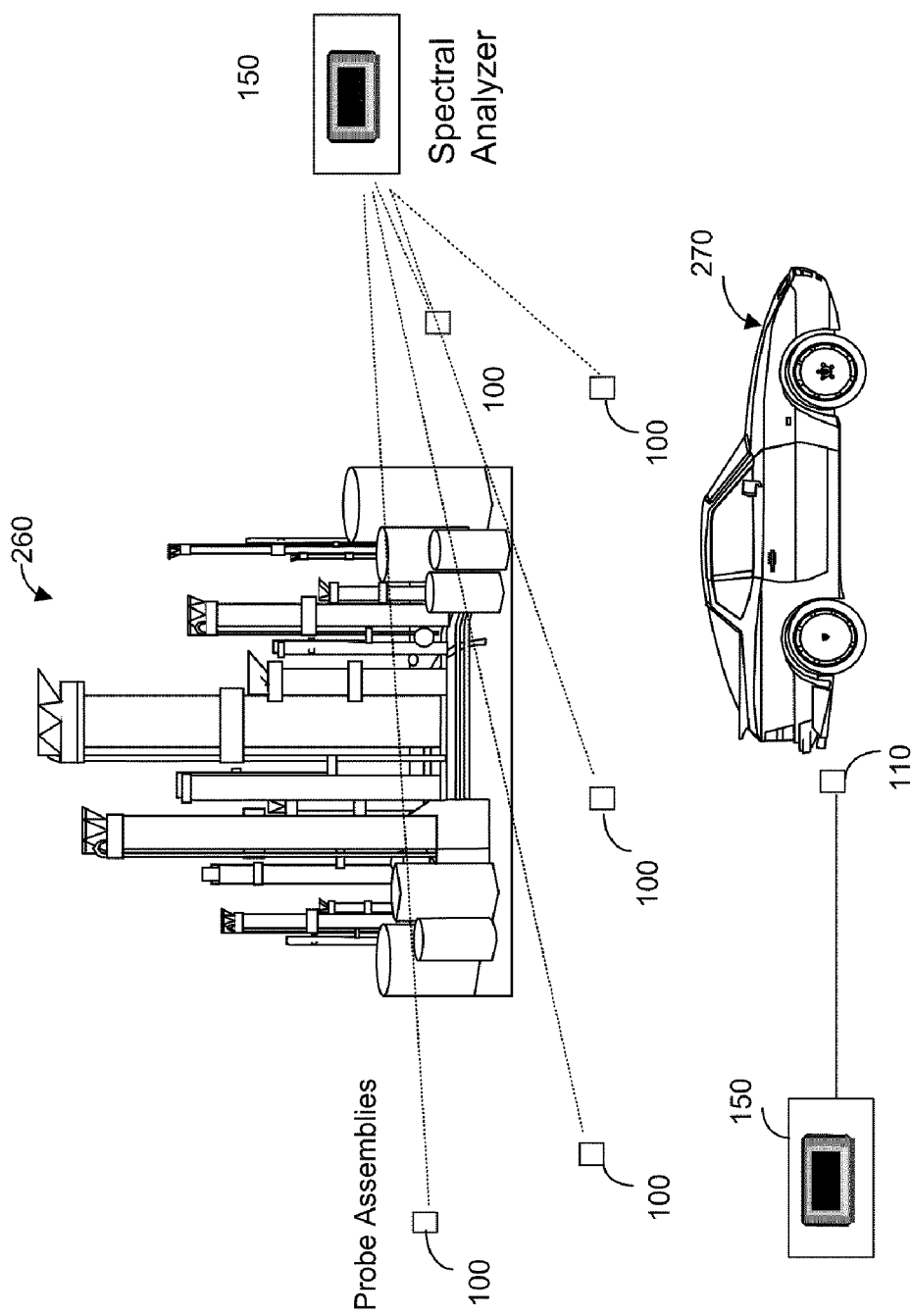
FIG. 5 is a schematic diagram showing environmental monitoring using a Raman scattering probe.

FIG. 5 is schematic diagram of applying the technology of Surface-Enhance Raman Scattering using a sensor to monitor harmful chemicals released into the environment. The light scattering probes 100 are distributed around potential pollution source, e.g., a factory 260 or around highway where great number of automobiles 270 pass through. The light scattering probes 100 distributed around the monitored areas generate Raman scattering light that is transmitted to a mainframe spectrum analyzer 150 to determine the contents and concentration of substance released into the environment. The monitoring sample can be, but not limited, soil, water, lake, river, seashore, well, plants, etc. This application can be extended to car exhausted gas detection and monitoring by placing the probe assembly near by car exhausting output.

Figure 6:
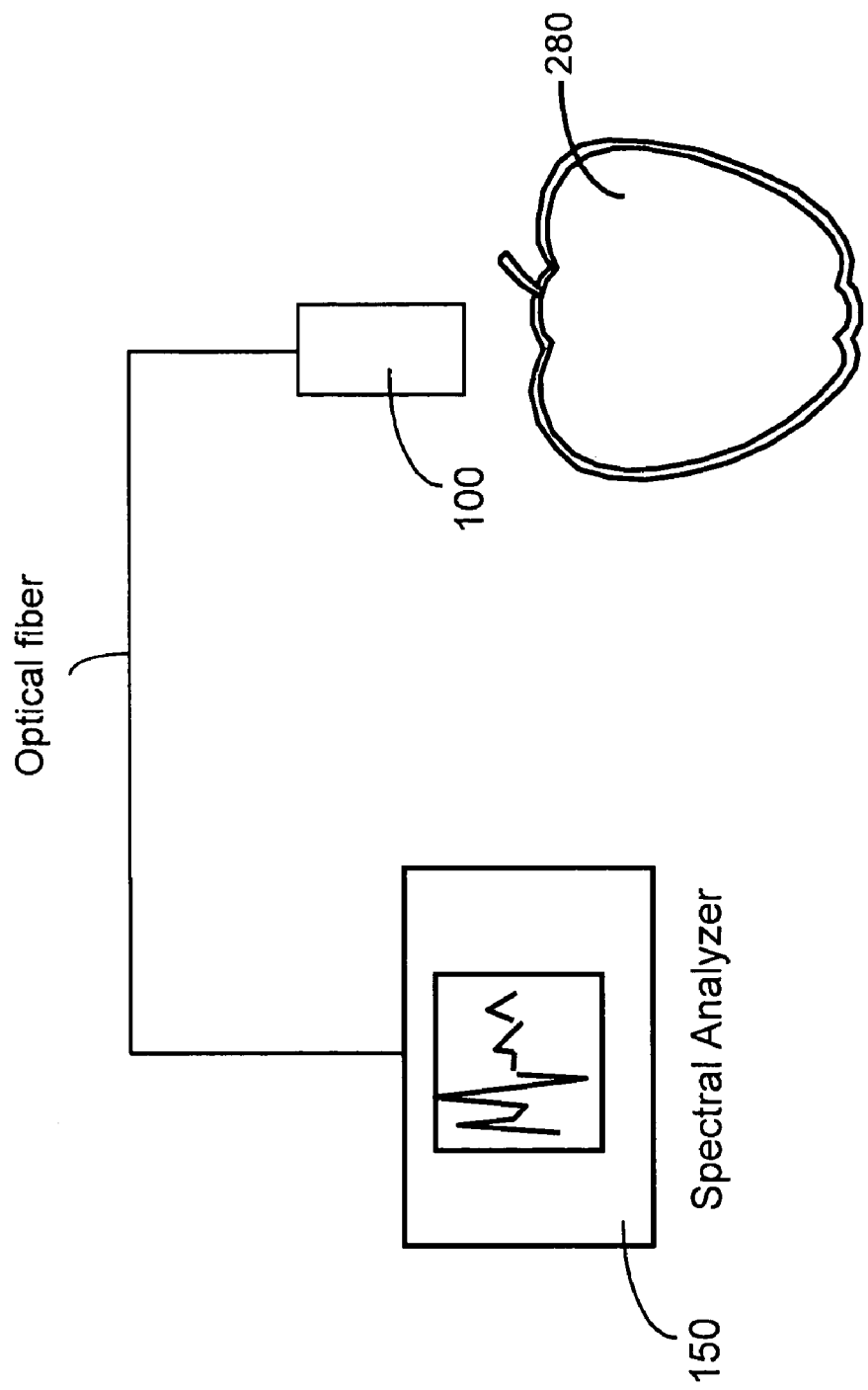
FIG. 6 is a schematic diagram showing inspection of food safety using a Raman scattering probe.

FIG. 6 is schematic diagram of applying the technology of Surface Enhance Raman Scattering using a sensor to monitor substances for inspecting quality and safety of foods. The light scattering probes 100 is placed close to a food item 280, i.e., an apple or different fruits, vegetables or other food items that could be contaminated through transportations, food processing, or even food growth process. The molecules of residue pesticide or other contaminations are drawn into the light scattering probe 100. A sensor is used to detect any suspect harmful chemicals contained in the food.

Figure 7:
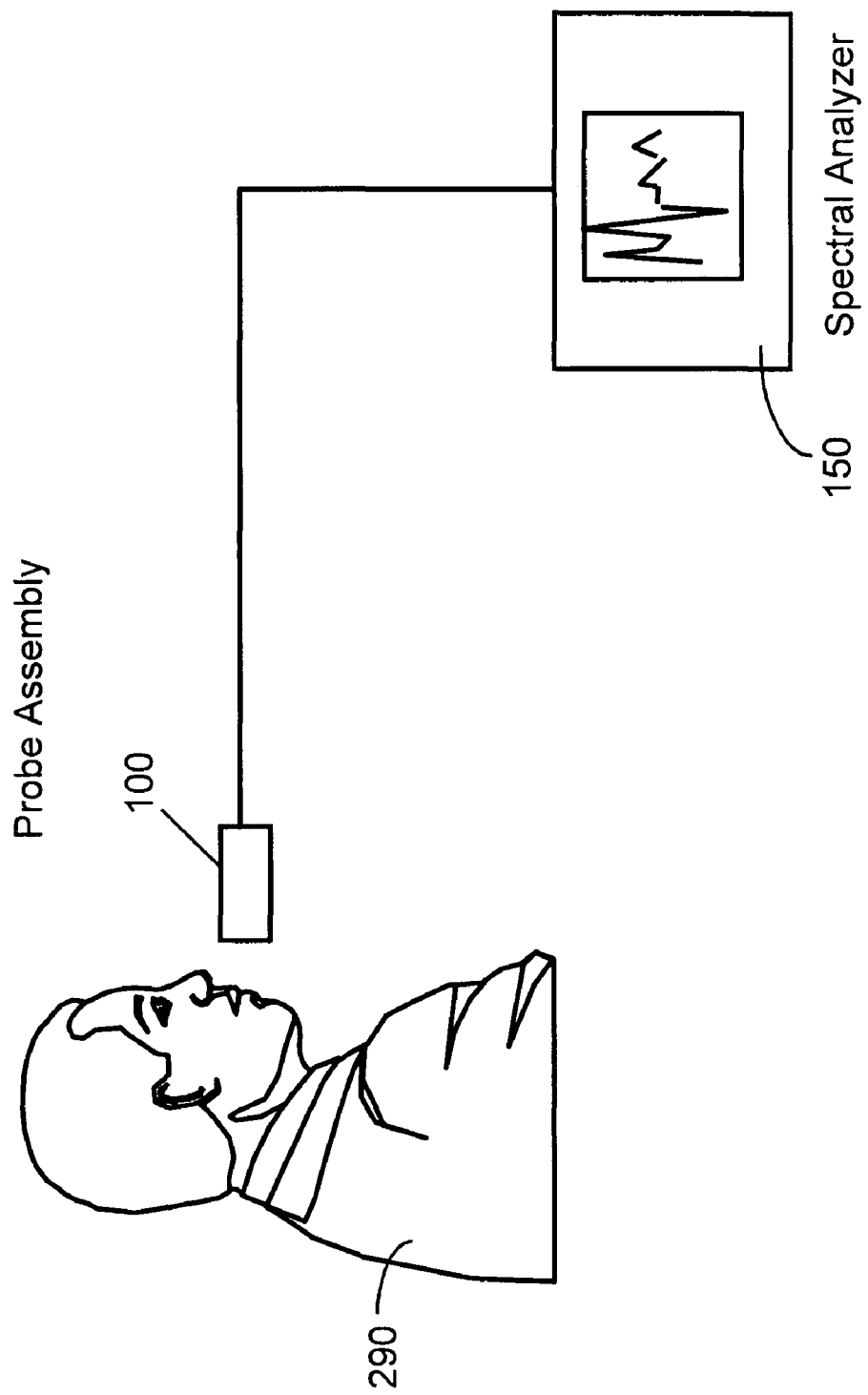
FIG. 7 is a schematic diagram showing disease diagnosis and biomedical detection using a Raman scattering probe.

FIG. 7 is schematic diagram of applying the technology of Surface Enhance Raman Scattering with or without using a sensor to monitor substances for early decease detection and diagnosis. The light scattering probe 100 is placed near a patient 290. Research result indicated that human breathed air have special chemicals contained, such as alkenes and benzene derivatives, if a person under screening is associated with disease, such as lung cancer. Raman sensing technology is able to fingerprint those chemicals in breath test to identify some special diseases such as cancers. The light scattering probe 100 is placed near the patient for carrying out a physical examination. The patient blows the outpoured breath-air to the light scattering probe 100. The sensor in probe assembly receives the inlet air for generating a Raman scattering light corresponding to the molecules contained in the airflow from the patient. The scattering lights are collected by probe head and sent to the spectral analyzer 150 to generate Raman spectrum. Breath test with Raman sensing technology is to make early disease diagnosis which disease includes, but not limited to lung cancer, breast cancer, stomach cancer, Liver cirrhosis, failing kidney, ulcer cancer, etc. In case of testing human body fluids, the fluid is dropped on a sensor manually, or Raman sensing device can be designed to connect to toilet for easy sample collection as smart toilet to timely monitor abnormal signals for disease and drug detection. This application also includes identifying and sorting protein, DNA and RNA. All testing samples in above applications can be placed in contact with a sensor to enhance the sensitivity and intensity of Raman scattering detections. The disclosed trace chemical detection using Raman light scattering can also be applied to other areas, including but not limited to identify Alzheimer's disease, non-invasively test glucose to monitor diabetes, non-invasive test carotenoids to monitor antioxidant status for early cancer screening purpose, and so on.

Figure 8:
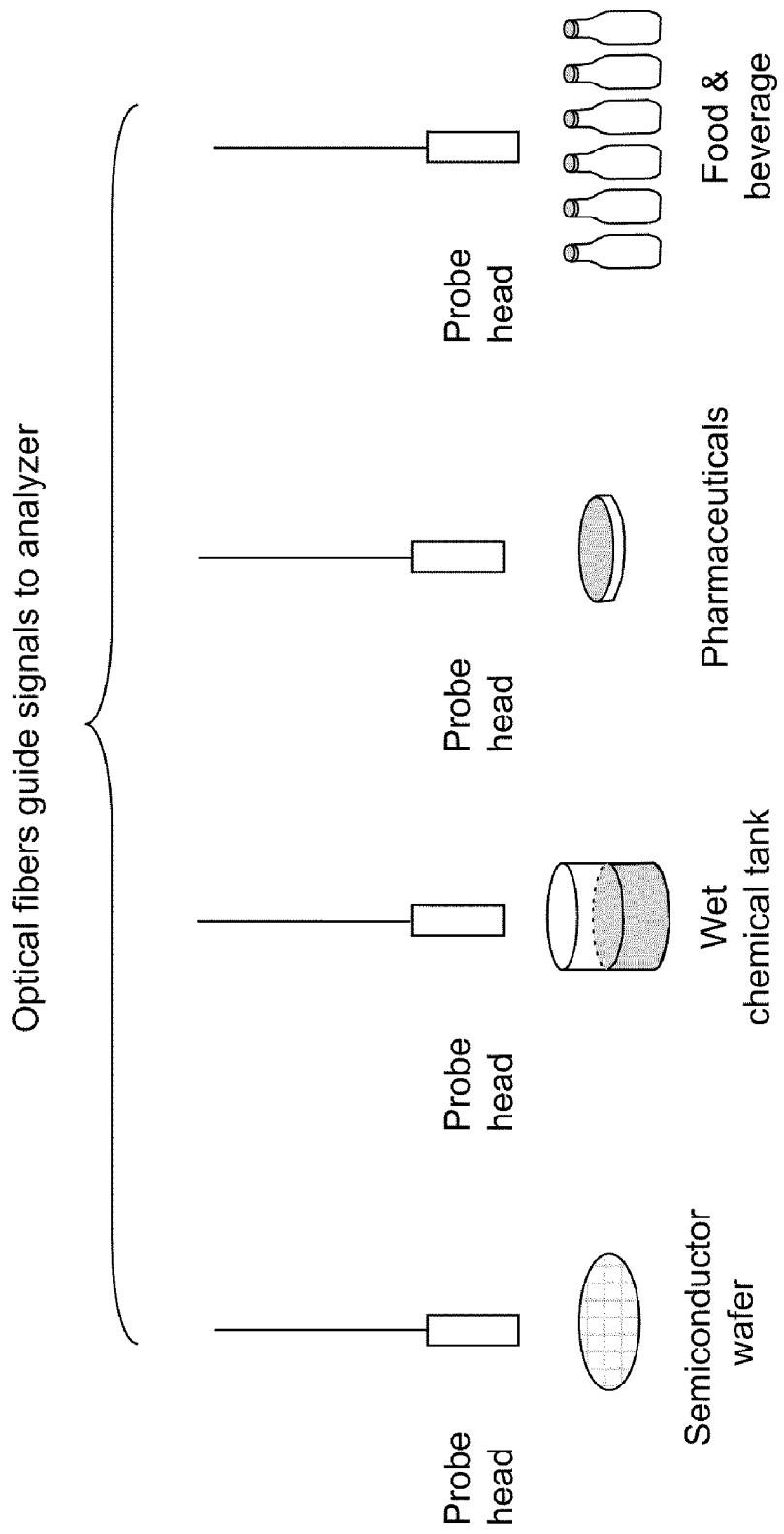
FIG. 8 is a schematic diagram showing manufacture quality control with and without a Raman scattering probe.

FIG. 8 is schematic diagram of Raman scattering application in industrial quality control with or without a sensor such as a RamanNanoChip™. The applications include, but are not limited to, the in-line monitoring wet chemical concentration in wet chemical process line, stand-off monitoring of sealed chemical tanks, remote trace chemical detection, semiconductor wafer defect evaluation, and monitoring of the food, fruit and vegetable storage, etc.

Figure 9:
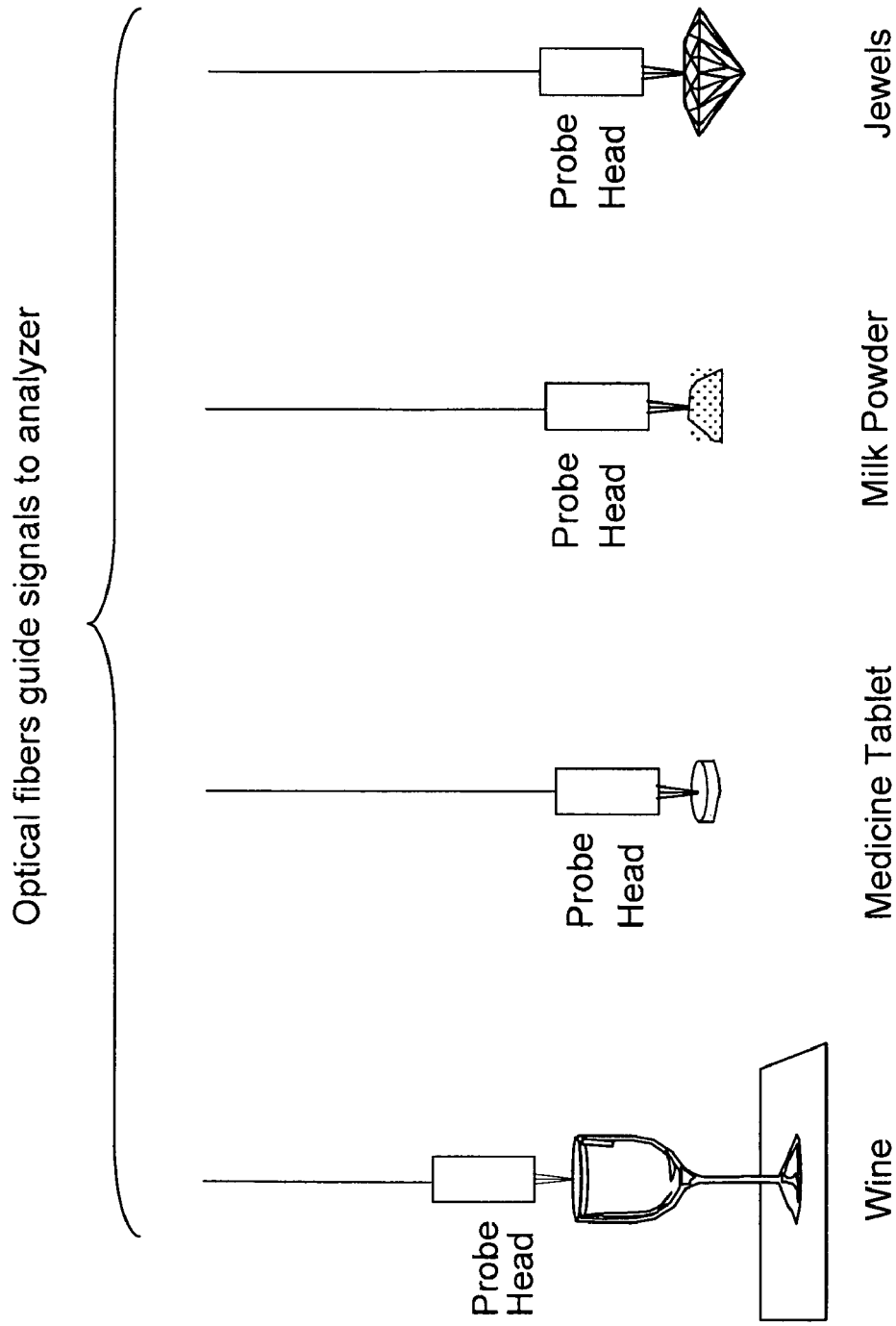
FIG. 9 is a schematic diagram showing detection of counterfeit merchandise, inspection of safety and quality food and beverages, and drug authentication using a Raman scattering probe.
Figure 10:
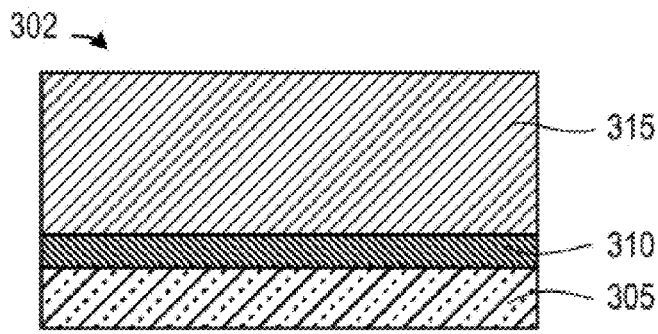
FIG. 10 is a cross-sectional view of a multi-layer layer structure to be used for fabricating a nano-structure.
Figure 11B:
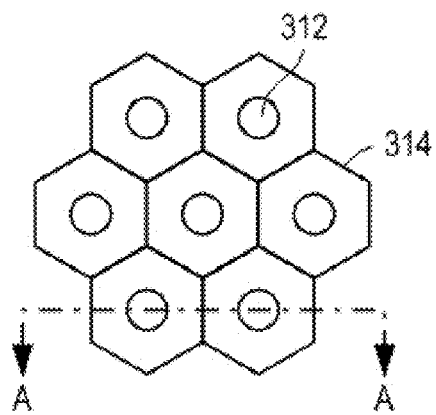
FIG. 11B is a top view of the multi-layer layer structure of FIG. 11A.
Figure 11A:
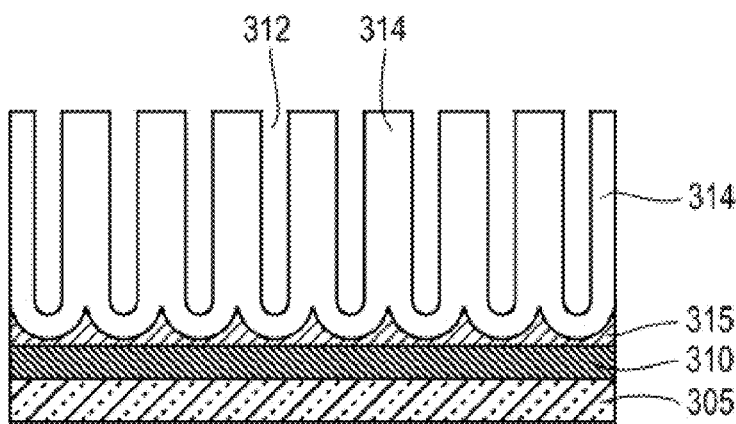
FIG. 11A is a cross-sectional view showing the formation of holes by anodization in the multi-layer layer structure of FIG. 10.
Figure 11C:
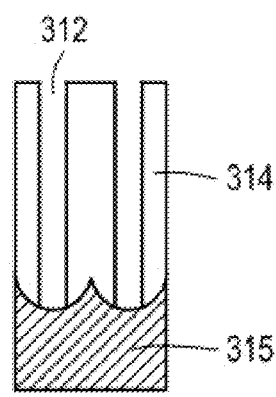
FIG. 11C is a cross-sectional view of the multi-layer layer structure along the line A-A in FIG. 11B.
Figure 12:
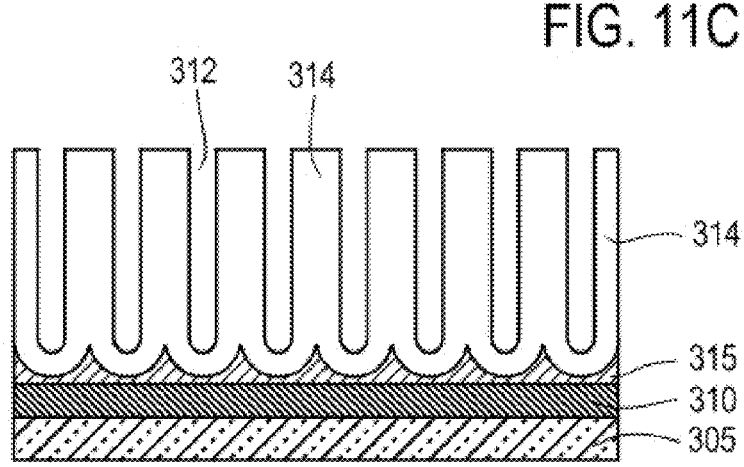
FIG. 12 is a cross-sectional view of the nano-structure formed on the multi-layer layer structure after a wet chemical etch or chemical mechanical polishing (CMP).

FIG. 9 is schematic diagram of applying the technology of Surface Enhance Raman Scattering to identify and screen materials for counterfeit merchandise and food safety screening. The applications may include operations such as food, drug and medicine screening. In theses cases, a sensor may or may not be required. The excitation laser directly strikes on samples under test. With improvement of the whole system of Raman Spectroscope, new applications that might not be available previously are now become practical. The Raman Spectrum of scattering light from the tested materials shows characteristic contents thus provide clear indications whether there are illegal additives added to the commercial merchandises. The potential counterfeit merchandise such as milkbased powder, wine, and medical tablets may be placed under the Raman detector as materials under investigation and screen. The applications can be extended to authenticated signatures and currency bills by detecting false signature and false bills by generating Raman scattering spectrum of the signature and dollar bills and compare these spectrum with measurements obtained from authenticated signature and dollar bills.

FIGS. 10 to 15 show a series of processing steps for fabricating a nano-structured noble metal surface of this invention. A multi-layer structure 302 (FIG. 10) includes a substrate 305, a conductive layer 310, and an aluminum oxide layer 315. The substrate 305 can for example be n-type silicon flat wafer (3-8 Ω-cm) or oxidized (30-50 nm SiO2) p-type silicon (5-10 mΩ-cm). The conductive layer 310 can include Ti and Ni and is deposited on the substrate 305 and can be electrically and thermally conductive. The thickness of the conductive layer 310 can be optimized to provide i) adhesion to a subsequently deposited noble metal film, such as Ag, or Au film, etc., ii) electrical conductive film to apply electrical bias to sensing surface in field application, iii) thermal conductive layer to apply lower temperature of sensing surface. The thickness of the conductive layer 310 can be typically controlled in the range of 100 Å-1,000 Å. Then The aluminum layer 315 is deposited on the conductive layer 310. The aluminum layer 315 can have a purity of 99.999% and thickness in the range of 1.0-10.0 µm. The substrate 305, the conductive layer 310, and the aluminum oxide layer 315 are annealed at 400° C.-500° C. in a $N_2$ purged furnace for 2-5 hours to recrystallize the Al film. Anodization is then conducted to produce a porous structure in a form of porous aluminum oxide layer 315 as that shown in FIGS. 11A and 11B. A porous structure is formed on the aluminum oxide layer 315 wherein the porous structure includes a plurality of pores 312 surrounded by walls 314 with the cross section view along a horizontal line A-A shown in FIG. 11C. Then wet oxide etch process is carried out in FIG. 12 to remove both top porous $Al_2O_3$ layer and barrier layer. A second anodization is carried out to consume all Al metal so that the barrier layer and top porous $Al_2O_3$ layer are right above the conductive metal layer.

Figure 13:
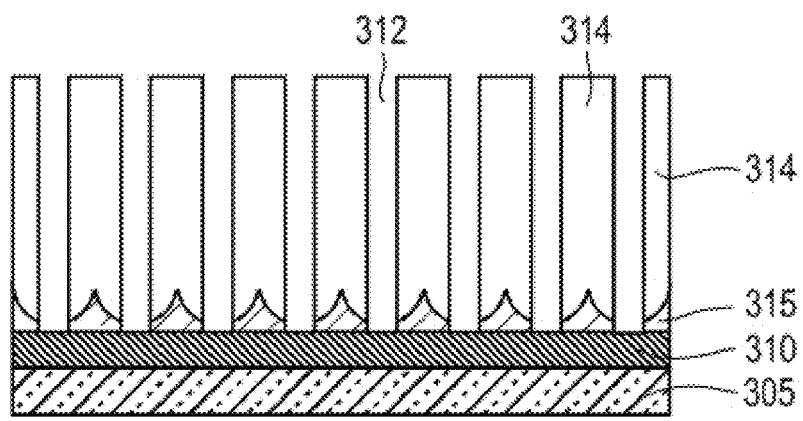
FIG. 13 is a cross-sectional view of the nano-structure formed on the multi-layer layer structure after the removal of the barrier layer at the bottom of the holes and etching down to the conducting layer.

In FIG. 13, an oxide etching is carried out to remove the barrier layer at the bottom of the pores and to widen the pore diameter. The wet etch process allows the pores 312 to extend downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) and the inter-pore distance (D) can depend on applied anodization voltage (V), current density (i) and the properties of the electrolyte, and the subsequent pore widening wet etch process.

Figure 14A:
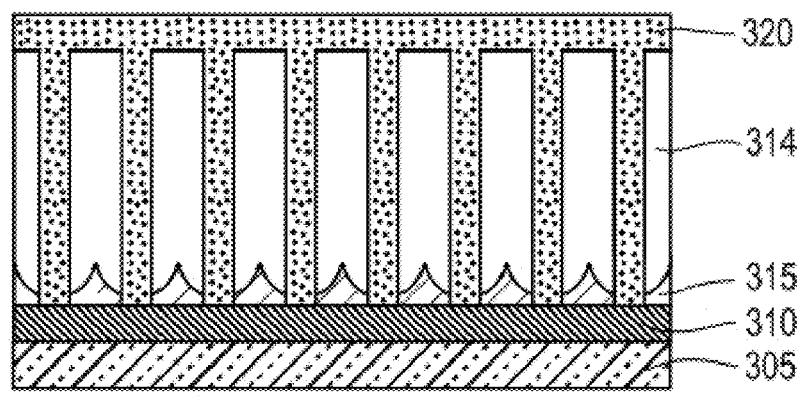
FIG. 14A is a cross-sectional view of the nano-structure formed on the multi-layer layer structure after the deposition of a noble metal.
Figure 14B:
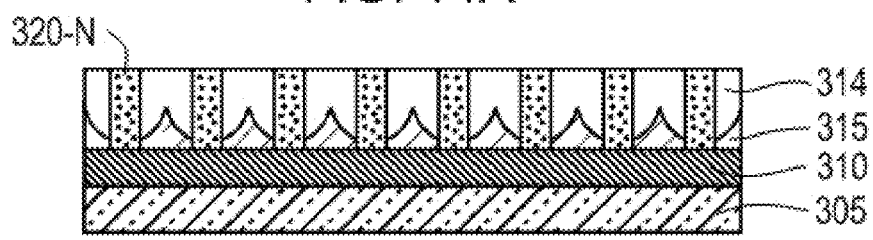
FIG. 14B is a cross-sectional view of the nano-structure formed on the multi-layer layer structure after the removal of the noble metal on the top layer.
Figure 15:
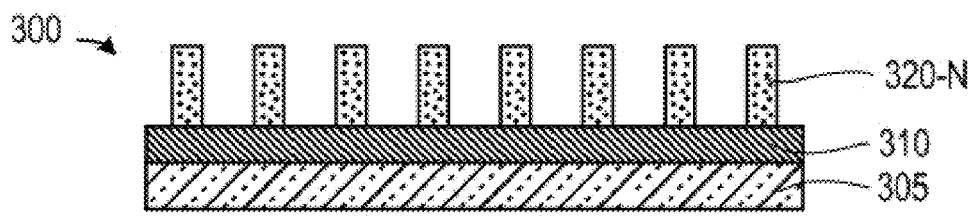
FIG. 15 is a cross-sectional view of the nano-structure formed on the multi-layer layer structure after the oxide layer is removed.

Referring to FIG. 14A, a noble metal such as Ag is deposited on the porous layer 315 to fill the pores 312 and to form a layer 320. The layer 320 can be formed by PVD process or electroplating. In FIG. 14B, a layer of the noble metal 320 is removed while leaving the noble metal 320-N in the pores 312. Another wet metal etch or CMP process is applied further control height of the noble metal 320-N filling the pores. In FIG. 15, the aluminum oxide 315 and the residue aluminum film 315-AL at the bottom of the porous aluminum layer 315 are removed to form a nano-structured surface 300 comprising an array of nano rods 320-N.

The nano rods 320-N are substantially straight and are perpendicular to the substrate 305 and the conductive layer 310. The nano rods 320-N can have substantially the same or similar widths. The neighboring nano rods 320-N are separated by gaps that remain substantially constant at different distances from the conductive layer 310.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc., that will be further described in a different patent application.

In some embodiments, nano-structures can be fabricated by a different process as shown in FIGS. 16A to 16F. A two-layer structure 362 includes a conductive layer 335 and a substrate 330. The conductive layer 335 can be made of titanium (Ti) or nickel (Ni), and can be electrically and thermally conductive. The substrate 330 can be an n-type silicon flat wafer (3-8 Ω-cm) or oxidized (30-50 nm $SiO_2$) p-type silicon flat wafers (5-10 mΩ-cm). The thickness of this conductive metal layer 335 can be controlled in the range of 100 Å-1,000 Å. An adhesion layer (e.g. made of Ag) can be deposited to the metal layer 335. The thickness of the conductive layer 335 can be optimized for applying an electric bias to the sensing surface for trace chemical detection and further for applying a lower temperature to the sensing surface to enhance sensitivity of trace chemical detection.

Figure 16A:
FIGS. 16A-16D, 16G, and 16H are cross-sectional views of the nano-structure formed on the multi-layer layer structure after the fabrication process.
Figure 16D:
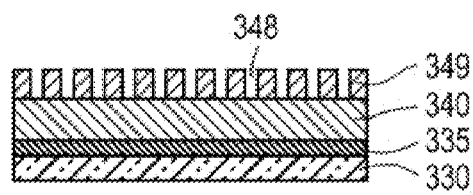
Figure 16B:
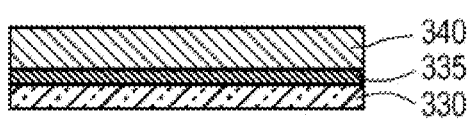

In FIG. 16B, a noble metal layer 340 is deposited on top of the conductive layer 335. The noble metal may be a silver layer, e.g., Ag layer having a thickness of 10-200 nm. In FIG. 16C, a second metal layer 345 is deposited on top of the noble metal layer 340. The second metal layer 345 can include aluminum with a 99.999% purity and a thickness in the range of 1.0-10.0 µm. The aluminum layer 345 is then annealed at 400° C.-500° C. in a $N_2$ purged furnace for 2-5 hours to recrystallize the Al film.

In FIG. 16D, an anodization process is carried out to produce a porous structure in a form of porous aluminum oxide 345'. A top view is shown in FIG. 16E where the porous structure is formed with naturally self-assembled hexagon-shaped nano pore-array that includes a plurality of pores 348 surrounded by hexagon-shaped pore wall 349. Neighboring pores 348 have a center-to-center distance D. After removing top anodized layer and the barrier layer by a wet chemical process, a second anodization process is carried out to consume all Al metal so that the barrier layer and top porous $Al_2O_3$ layer 345' are right above the noble metal layer 340. Then a wet etch process is performed to widen the pores 348 and to remove the barrier layer at the bottom of the pores 348. As the wet etch process proceeds, as shown in FIG. 16F, the pores 348 are widened and the walls 349 surrounding the pore become thinner. The etch process can be controlled to form a plurality of nano-holes 348 surrounded by wall 349. Alternatively, the etching of the pores 348 can widen the pores 348 so much such they touch each other, which can produce a hexagonal array of quasi-triangle nano columns 349'.

Figure 16G:
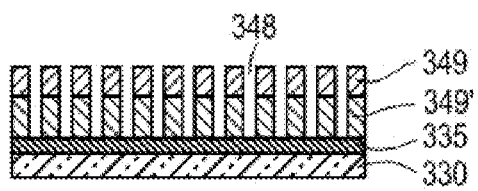
Figure 16C:
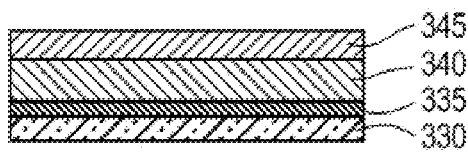
Figure 16H:
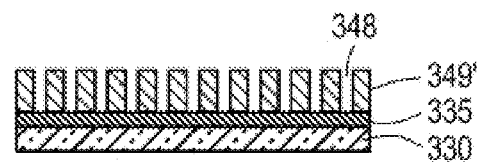
Figure 16F:
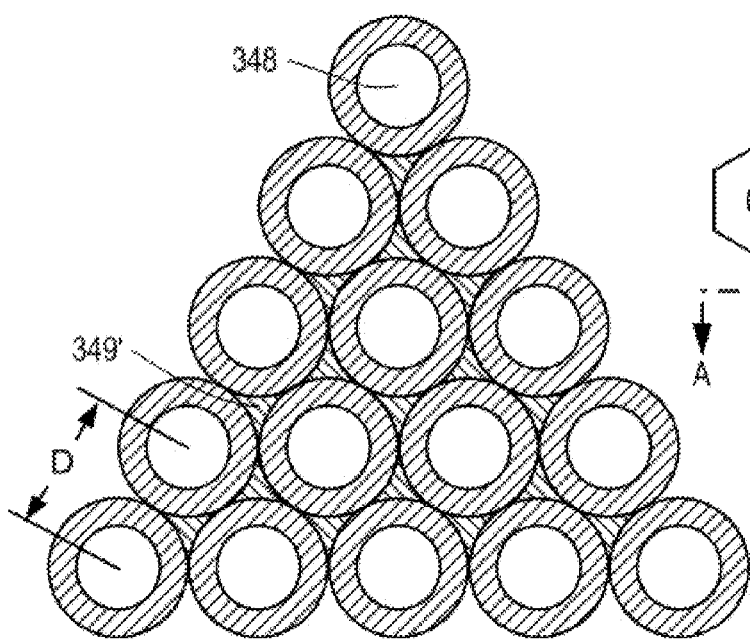
FIGS. 16E and 16F are top views of the nano-structure formed on the multi-layer layer structure after the fabrication process.
Figure 16E:
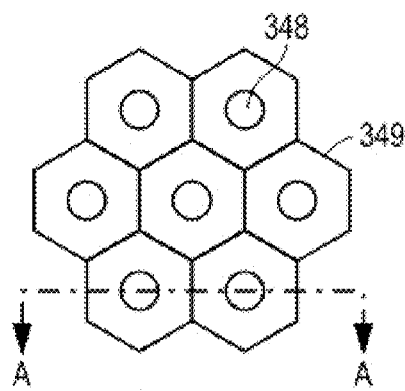

In FIG. 16G, the noble metal layer 340 is etched down and the pores 348 are extended downward to reach the conductive titanium layer 335. In FIG. 16H, a wet oxide etch is performed to remove the aluminum oxide followed by a wet metal etch to remove the aluminum residue at the bottom of the pores 348. The aluminum oxide 315 and the residue aluminum film 315 at the bottom of the porous aluminum layer 315 are removed to form an array of nano rods 349' having controlled heights, diameters and well-defined inter-rod distances. The array can have quasi-triangle periodic cells.

The nano rods are substantially straight and are substantially perpendicular to the substrate 330 and the conductive layer 335. The nano rods can have substantially the same or similar widths. Neighboring nano rods are separated by gaps that remain substantially constant at different distances from the conductive layer 335.

In some embodiments, nano surface structures can be prepared by coating the surface of the sensor 105 by a solution containing a colloidal suspension of nano particles. The nano particles can be formed by a metallic materials (such as Au, Ag, etc), oxide material (such as Titanium oxide, silicon oxide, zinc oxide, etc), or a polymeric material. Oxide or polymeric particles can be doped with metal ions or coated with a conductive material. The colloidal suspension can include single nano particles or clusters of nano particles. A nano surface structure is formed after the solution applied to the sensor surface. The solution can evaporate, leaving the nano particles adsorbed with the target molecules on the sensor surface.

Figure 17:
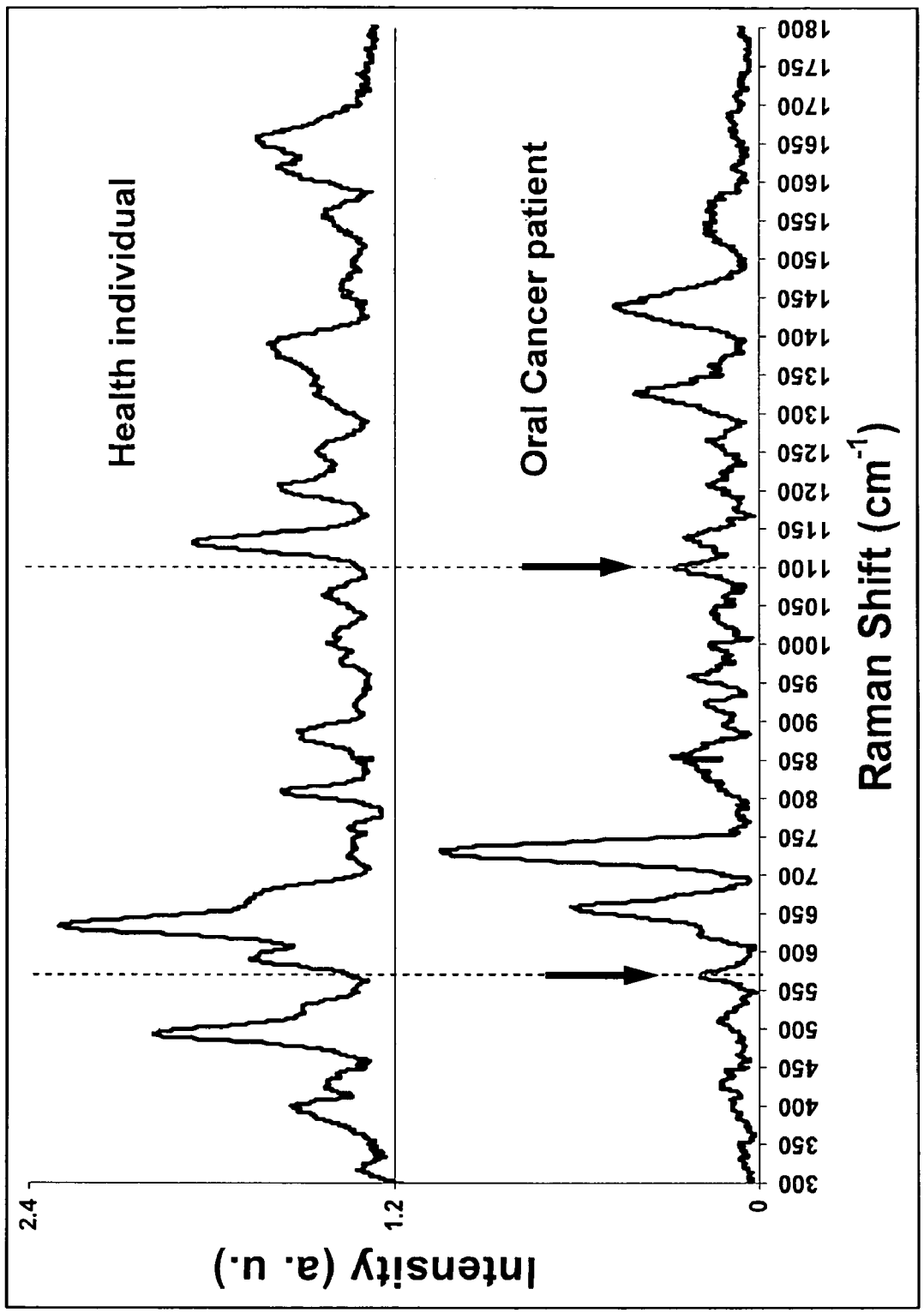
FIG. 17 illustrates an exemplified Raman spectral signature for oral cancer detected in the saliva of an oral cancer patient by the disclosed Raman scattering probe.

In some embodiments, diseases can be identified by analyzing Raman spectra obtained from body fluids from a patient using the light scattering probe 100 as described above. Referring to FIG. 17, the Raman spectrum obtained from a saliva sample from an oral cancer patent has show two signature spectral peaks respectively around, for example, 560 $cm^{-1}$ (in the region from 530 $cm^{-1}$ to 570 $cm^{-1}$) and 1100 $cm^{-1}$ (in the region from 1185 $cm^{-1}$ to 1105 $cm^{-1}$) which are absent in a healthy individual without the oral cancer. The signature spectral peaks at 560 $cm^{-1}$ and 1100 $cm^{-1}$ are associated with molecular vibrations for C—S, S—S, and O—P—O($PO_2$) bonds in, for example, cysteine, ATP, ADP, and other phosphate containing biological samples. The identification of these spectral signatures can include the steps: a spectral band is first selected at Raman peaks with Raman shift in unit of $cm^{-1}$ (wave number) of each spectral signature. A background scattering intensity level is determined. The peak intensity level, relative intensity or integrated area of the peak, is calculated. A signal-to-noise ratio is calculated using the peak intensity and the background level. If the signal-to-noise ratio is higher than a predetermined threshold (e.g., 3 or higher), the spectral signature of a Raman peak is positively identified. The identification of spectral signatures for detecting diseases and drug use can be assigned by statistical analysis and several computation algorithms such as dendrograph classification and Principal Component Analysis. A patient can be diagnosed as likely having oral cancer or at an early stage of an oral cancer if spectral signatures around 560 $cm^{-1}$ and 1100 $cm^{-1}$ are both identified. Appropriate doctors and patients themselves may be alerted for further testing using the same or other types of diagnosis techniques.

Figure 18:
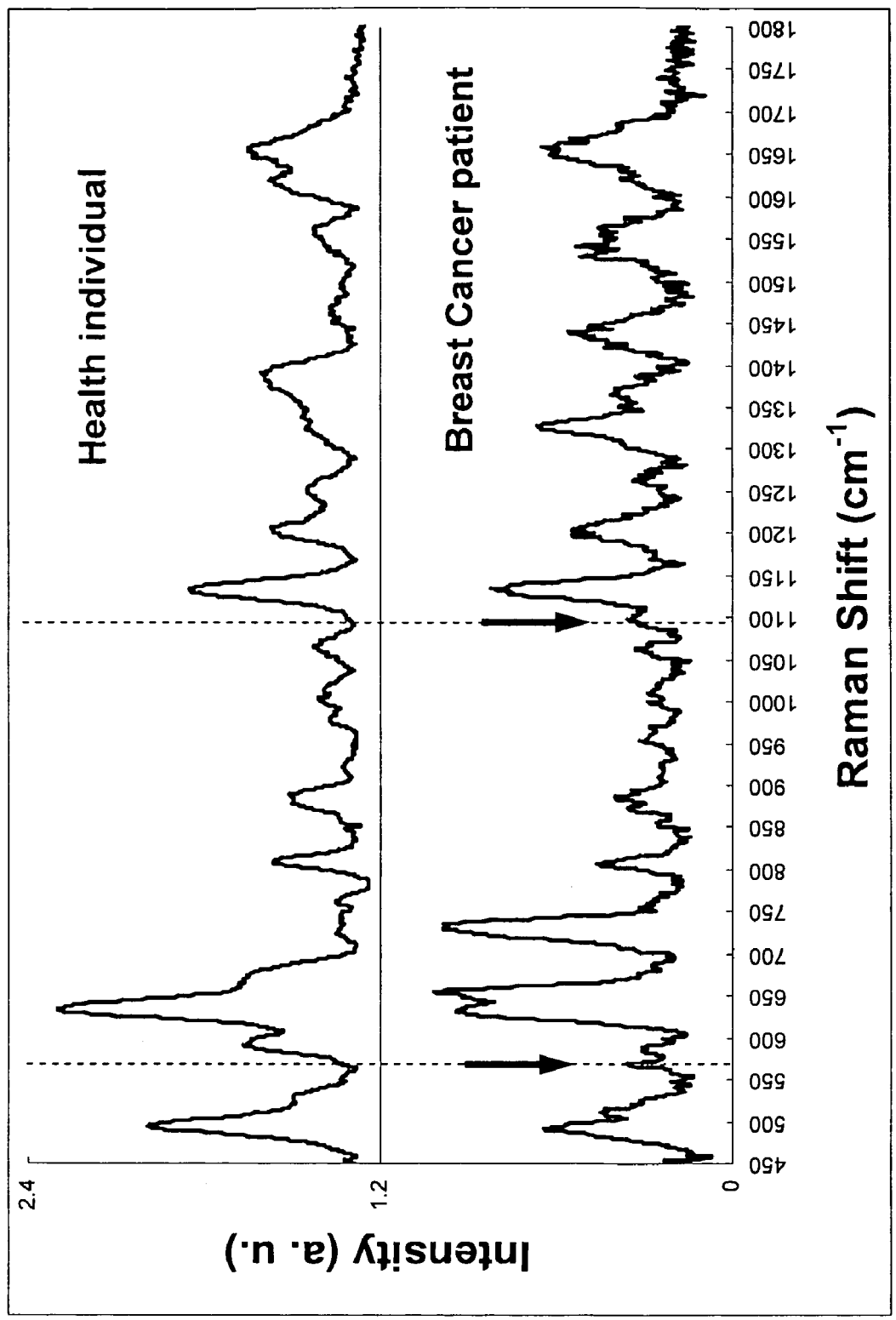
FIG. 18 illustrates an exemplified Raman spectral signature for breast cancer detected in the saliva of a breast cancer patient by the disclosed Raman scattering probe.
Figure 19A:
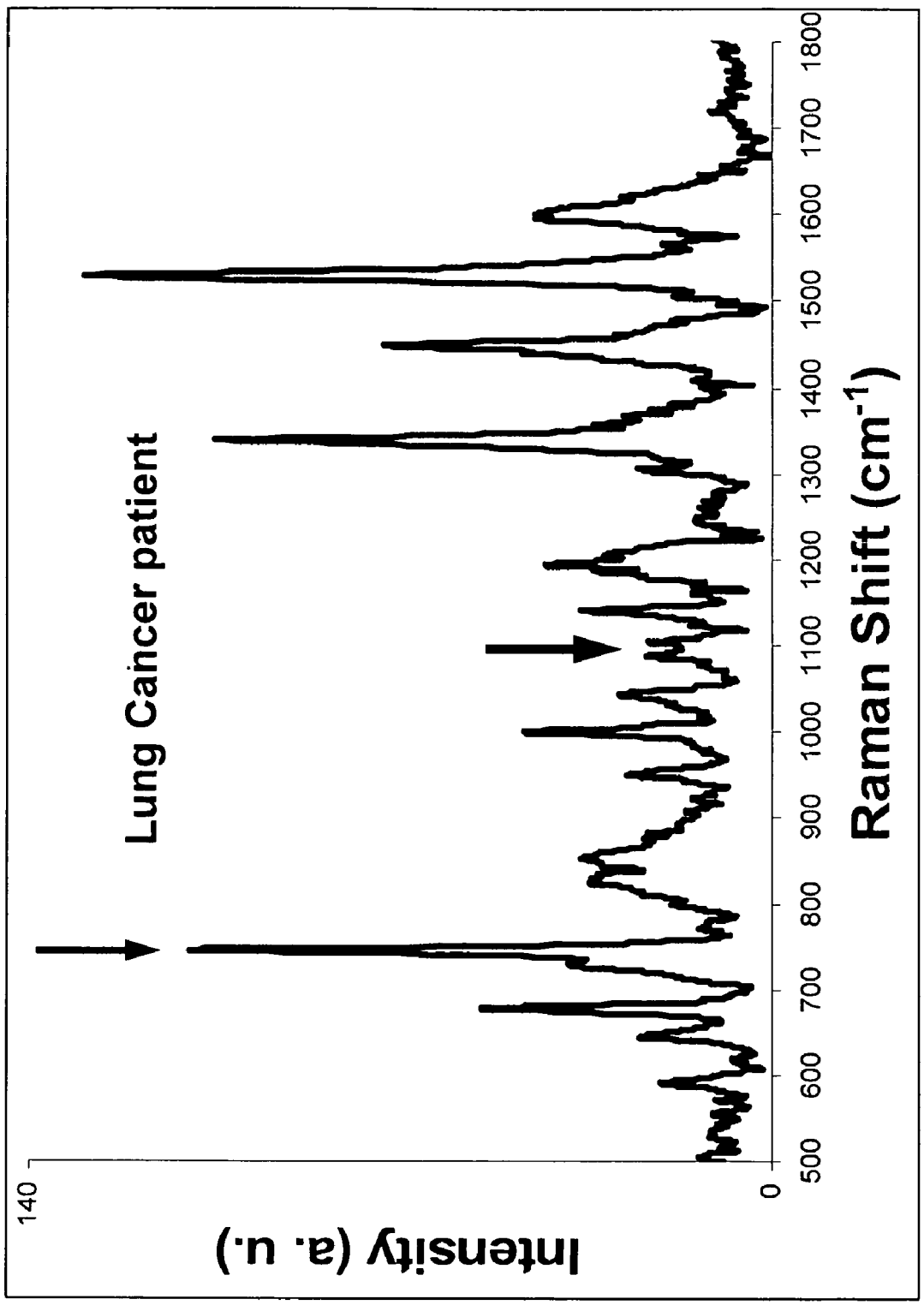
FIGS. 19A and 19B illustrates an exemplified Raman spectral signature for lung cancer detected in both the saliva and the serum of a lung cancer patient using the disclosed Raman scattering probe.
Figure 19B:
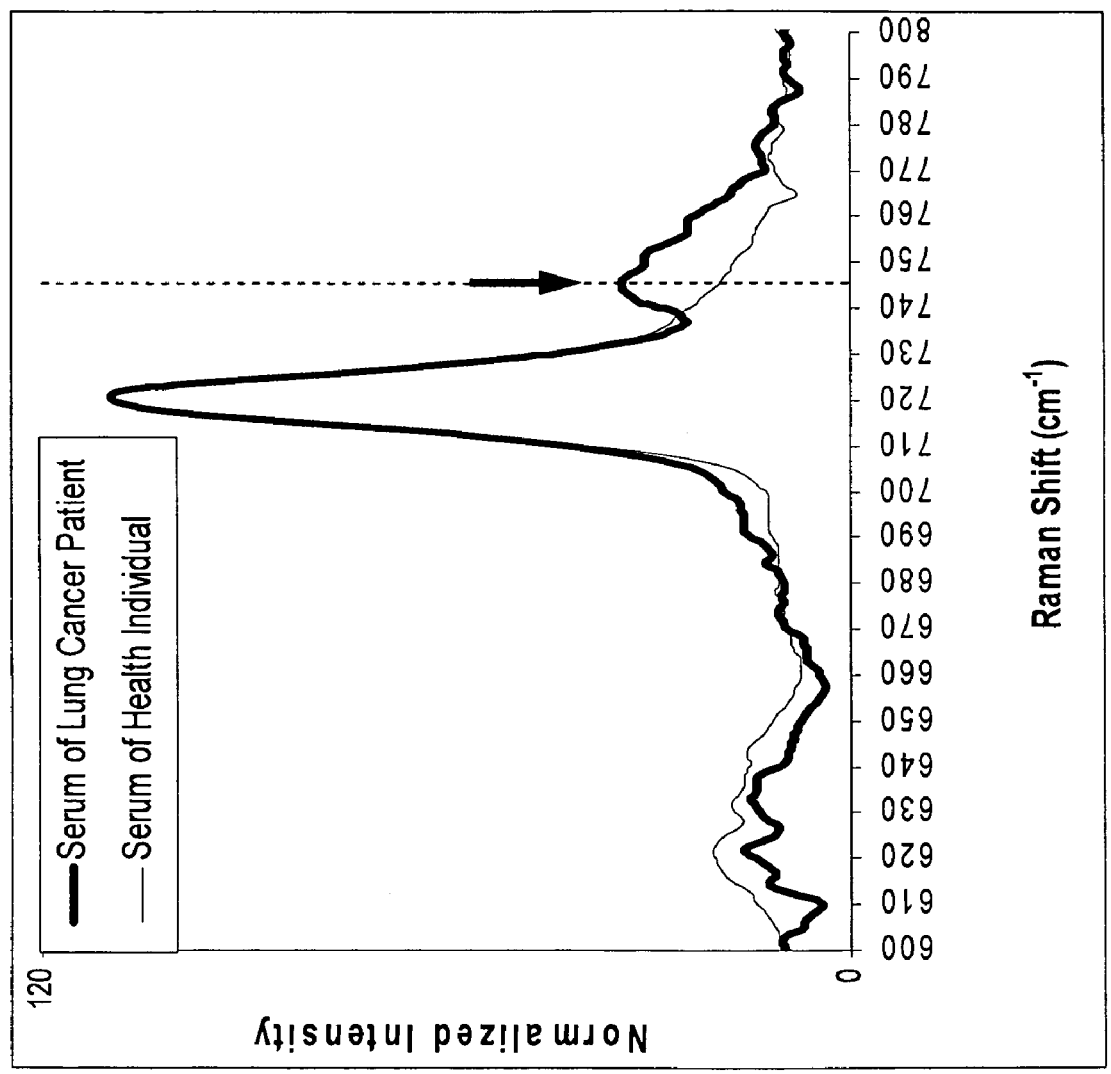
Figure 20:
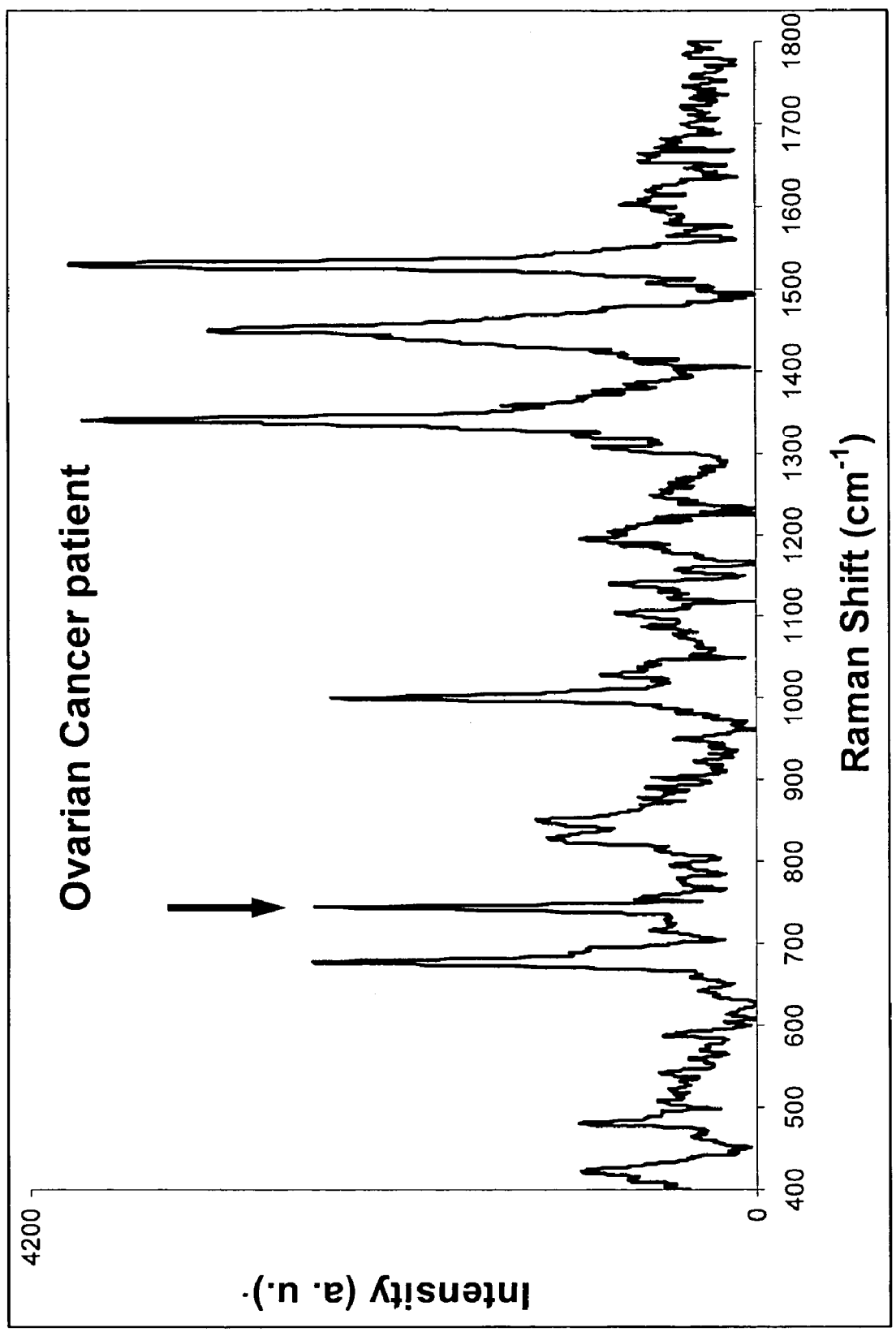
FIG. 20 illustrates an exemplified Raman spectral signature for ovarian cancer detected in the serum of a ovarian cancer patients by the disclosed Raman scattering probe.
Figure 21:
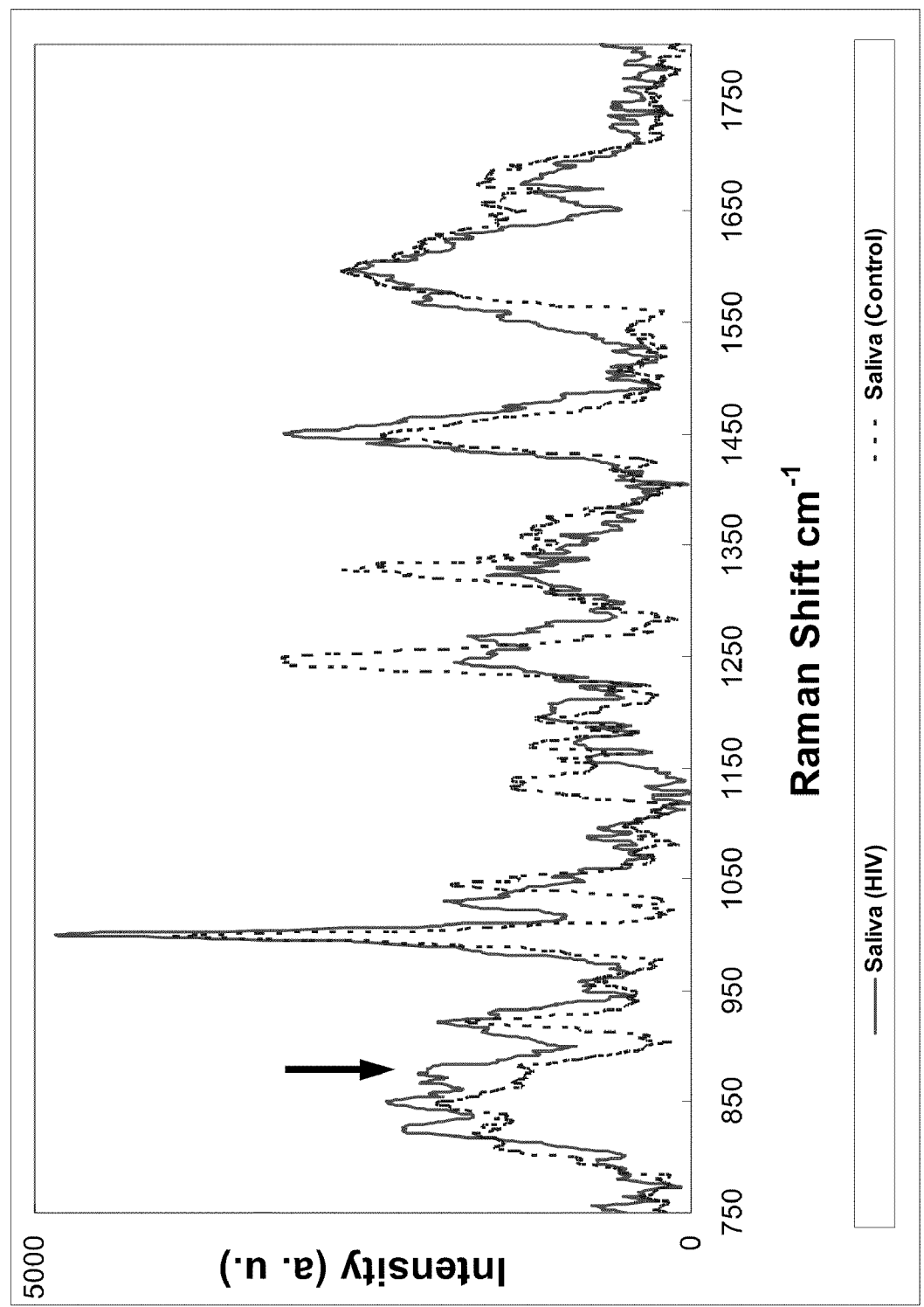
FIG. 21 illustrates an exemplified Raman spectral signature for HIV detected in the saliva of an HIV patient by the disclosed Raman scattering probe.
Figure 22:
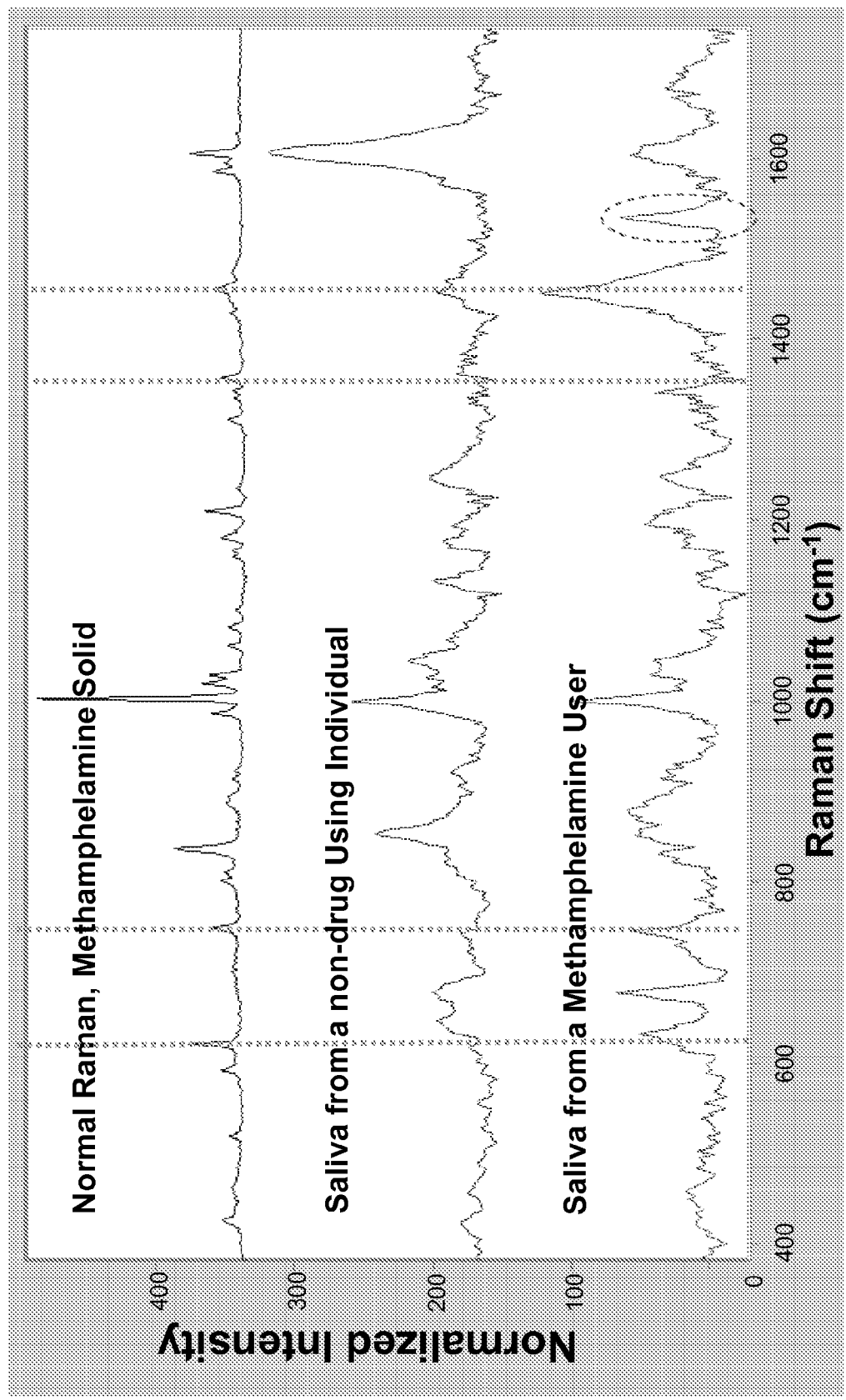
FIG. 22 illustrates an exemplified Raman spectral signature for illicit drug use detected in the saliva of an illicit drug user by the disclosed Raman scattering probe.

The disclosed systems and methods can also be used to estimate glucose level so that to evaluate diabetes status. A signature spectral peak in the region from 1115 $cm^1$ to 1135 $cm^{-1}$, for example, 1124 $cm^{-1}$, which is associated with molecular vibration of glucose, in a Raman spectrum obtained from a saliva sample from a diabetes patient can provide key evidence for diagnosing diabetes. The intensity, relative intensity or integrated area of this Raman peak, can be used to evaluate glucose concentration of a body fluid from a patient to score potential diabetes level. Similarly, referring to FIGS. 18-20, breast cancer can also show spectral signatures in Raman spectrum obtained from saliva around 560 $cm^{-1}$ and 1100 $cm^{-1}$ (FIG. 18). Saliva and serum samples obtained from lung cancer and ovarian cancer patients can have a Raman spectral signature around 745 $cm^{-1}$ (FIGS. 19 and 20). The signature spectral peak at 745 $cm^{-1}$ is associated with molecular vibrations for C—S bonds in phosphate. HIV can have a spectral signature in Raman spectrum obtained from a serum sample in the region of 865 $cm^{-1}$-885 $cm^{-1}$, for example, around 870 $cm^{-1}$ (FIG. 21). The disclosed systems and methods can also be used to identify illicit drug such as heroin, methamphetamine cocaine, caffeine, morphine, codeine, amphetamine, ephedrine, papaverine, narcotine, MDMA, etc. FIG. 22 shows Raman spectra from a methamphetamine solid (a type of illicit drug), a saliva sample of a non-drug using individual, and a methamphetamine drug user. The Raman spectrum from a drug-user's saliva sample shows a characteristic peak around 1030 $cm^{-1}$ and 1535 $cm^{-1}$, which can be used to indicate illicit drug use. The disclosed methods and systems can also be used to detect doping (e.g., hormone) in athletes during international sports competitions such as the Olympic Games.

Figure 23:
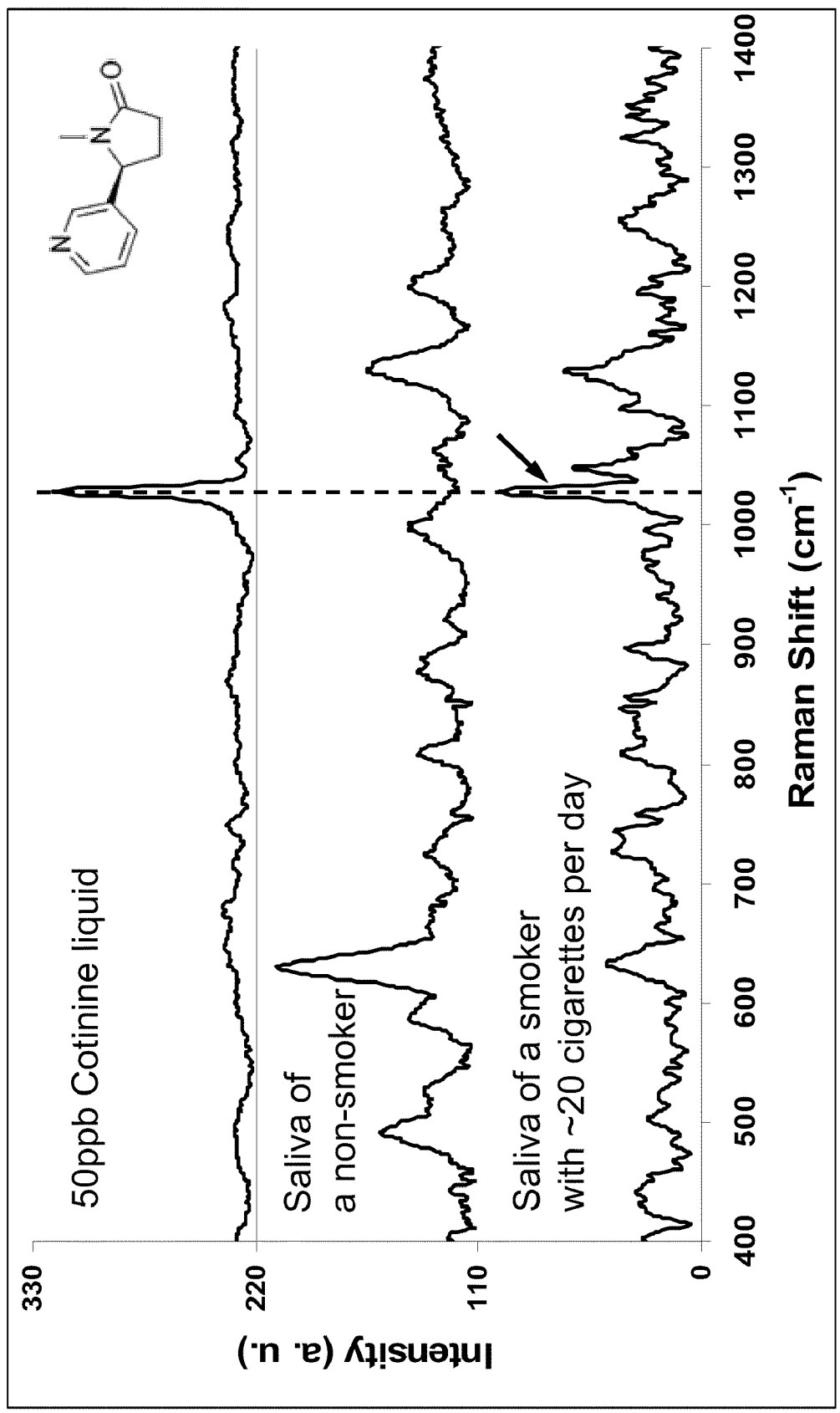
FIG. 23 illustrates an exemplified Raman spectral signature for the smoking status detected in the saliva of a smoker by the disclosed Raman scattering probe, with a comparison of an Raman spectral signature of the cotinine which is the metabolite of nicotine.

Similarly, referring to FIG. 23, smoking status or secondary smoking status can also show spectral signature at around 1029 $cm^{-1}$ in a Raman spectrum obtained from a saliva sample of a smoker, which is absent in a non-smoking healthy individual. The signature spectral peaks around 1029 $cm^{-1}$ is associated with molecular vibration mode of cotinine which is metabolite of nicotine.

Figure 24:
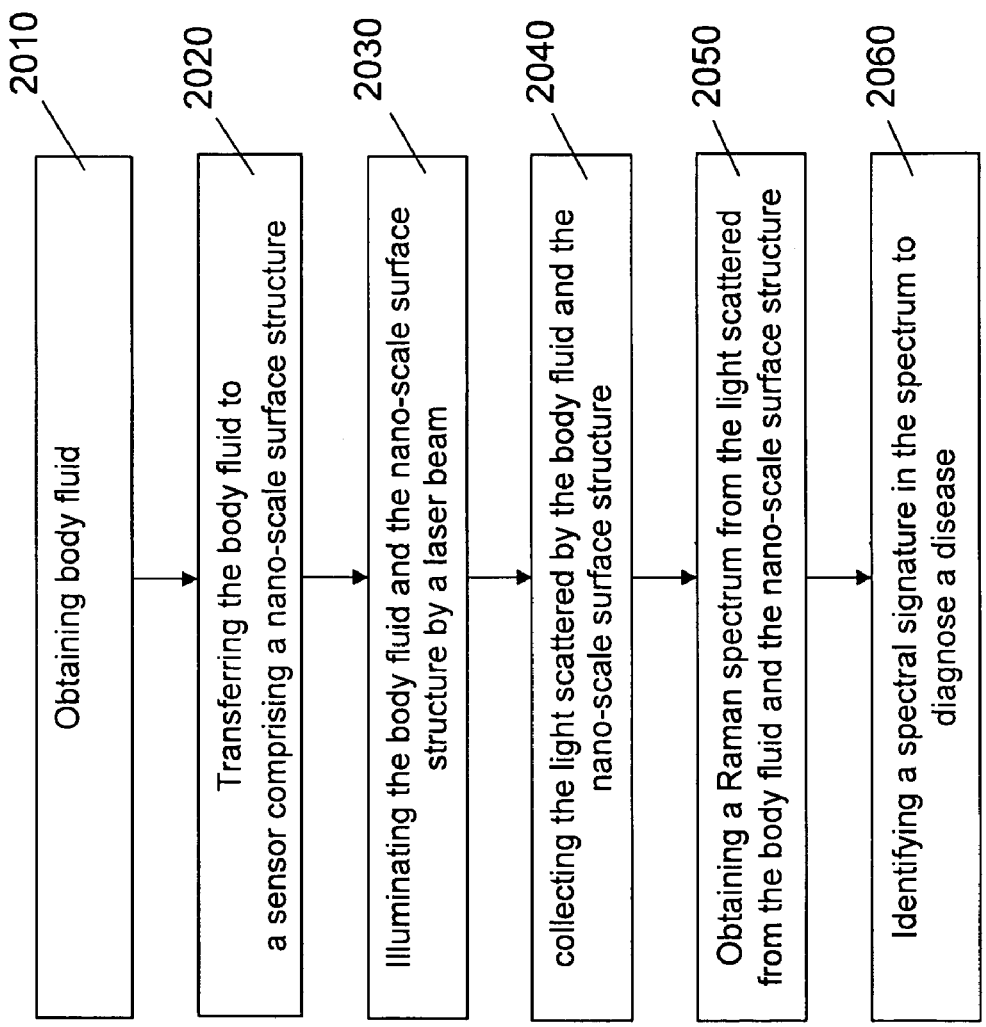
FIG. 24 is a flowchart for non-invasive disease diagnosis using the disclosed Raman scattering probe.

The non-invasive disease detection and diagnosis using the disclosed Raman scattering probe can include one of more of the following steps: referring to FIG. 24, a body fluid is first obtained from a patient or an illicit drug user (step 2010). Due to the high sensitivity of the disclosed Raman scattering sensors, the amount body fluid can be rather small. For example, the volume of the body fluid obtained from the patient can be in a range from about 100 pl to 1 ml. Examples of the body fluid can include blood, saliva, urine, serum, tear, sweat, and stomach fluid. After centrifuge, the body fluid is next transferred to a sensor (e.g., a RamanNanoChip™) comprising a nano-scale surface structure (step 2020). Molecules in the body fluid are adsorbed to the nano-scale surface structure. A laser beam is applied to illuminate the body fluid, the nano-scale surface structure, and the molecules adsorbed onto the nano-scale surface structure (step 2030). Light scattered by the body fluid, the nano-scale surface structure, and the adsorbed molecules is collected (step 2040).

A Raman spectrum is obtained from the scattered light (step 2050). One or more spectral signatures are identified in the spectrum to diagnose a disease (step 2060). Examples of the diseases that can be detected include lung cancer, breast cancer, stomach cancer, esophageal cancer, thyroid cancer, larynx cancer, liver cirrhosis, a failing kidney, ulcer cancer, ovarian cancer, uterus cancer, cervix cancer, oral cancer, leukemia, colon cancer, bladder cancer, prostate cancer, bronchus cancer, HIV, and drug addiction. As previously described, the one or more spectral signatures are at predetermined wavelengths in the Raman spectrum. The wavelengths and the characteristics of the spectral signatures are specific to the disease to be detected. For example, spectral signatures for oral and breast cancers in a saliva sample can be at around 560 $cm^{-1}$ or 1100 $cm^{-1}$. A spectral signature for lung cancer in a serum sample can be at around 745 $cm^{-1}$ in the Raman spectrum. A spectral signature can include a spectral peak. The spectral signature can be identified when the spectral peak is above certain threshold. For example, a signal-to-noise ratio of the spectral peak relative to the noise background can be above 3 for the spectral signature to be positively identified.

In some embodiments, the disclosed light scattering probe and disclosed chemical detection methods can be applied in food safety applications, which can include screening illegal additives and verifying useful ingredients in food products. An example for food products is dairy products. Dairy products can include milk, milk powders (e.g., baby formula), cheese, cheese-containing cakes, yoghurts, ice creams, milk containing candies, milk contained food products, and protein contained food products. A recent serious issue in food safety is related to illegal melamine additive in dairy products such as baby formula, ice cream, and biscuit, etc. The disclosed methods and systems are also applicable to detecting existence and levels of methanol, in alcohol products such as wines, nitrite, sodium cyclamate (sodium cyclohexylsulfamate) and other food additives in food, beverage, alcohol products such as red wine, and wine.

As described above in relation to FIGS. 1, 8 and 9, milk sample solutions are prepared from a milk solution by respectively applying with melamine additive at concentrations of 1 ppm (parts per million), 2 ppm, 5 ppm, and 50 ppm. The milk sample solutions are separately applied to a sensor (105 in FIG. 1) and Raman spectra are obtained using the light scattering probe and method described above. A typical volume for the food sample solution is in a range from about 100 pl to 1 ml.

Figure 25A:
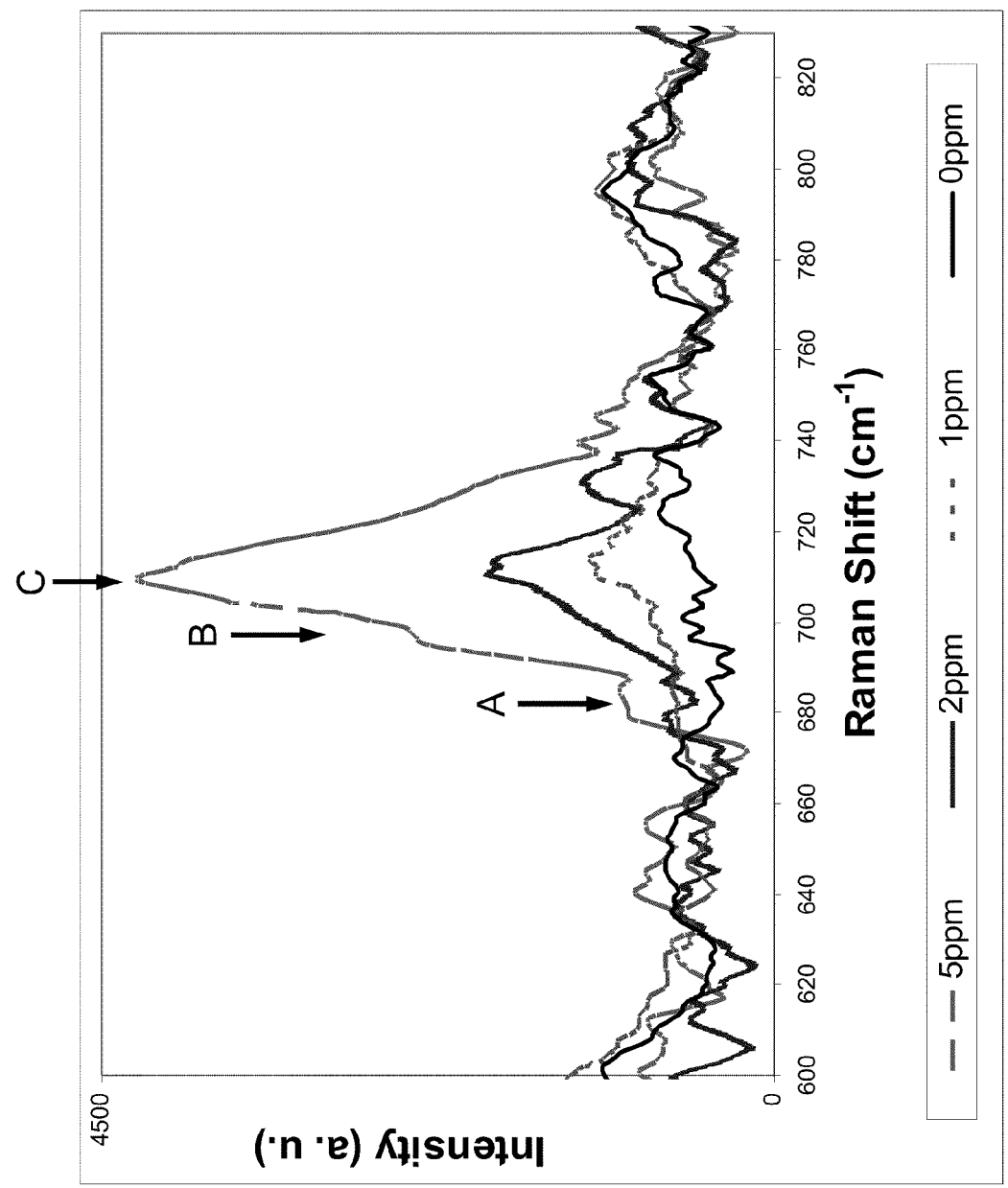
FIGS. 25A and 25B illustrate Raman spectra having spectral signatures for an illegal and harmful chemical (melamine) detected at different concentration levels in a milk product.
Figure 25B:
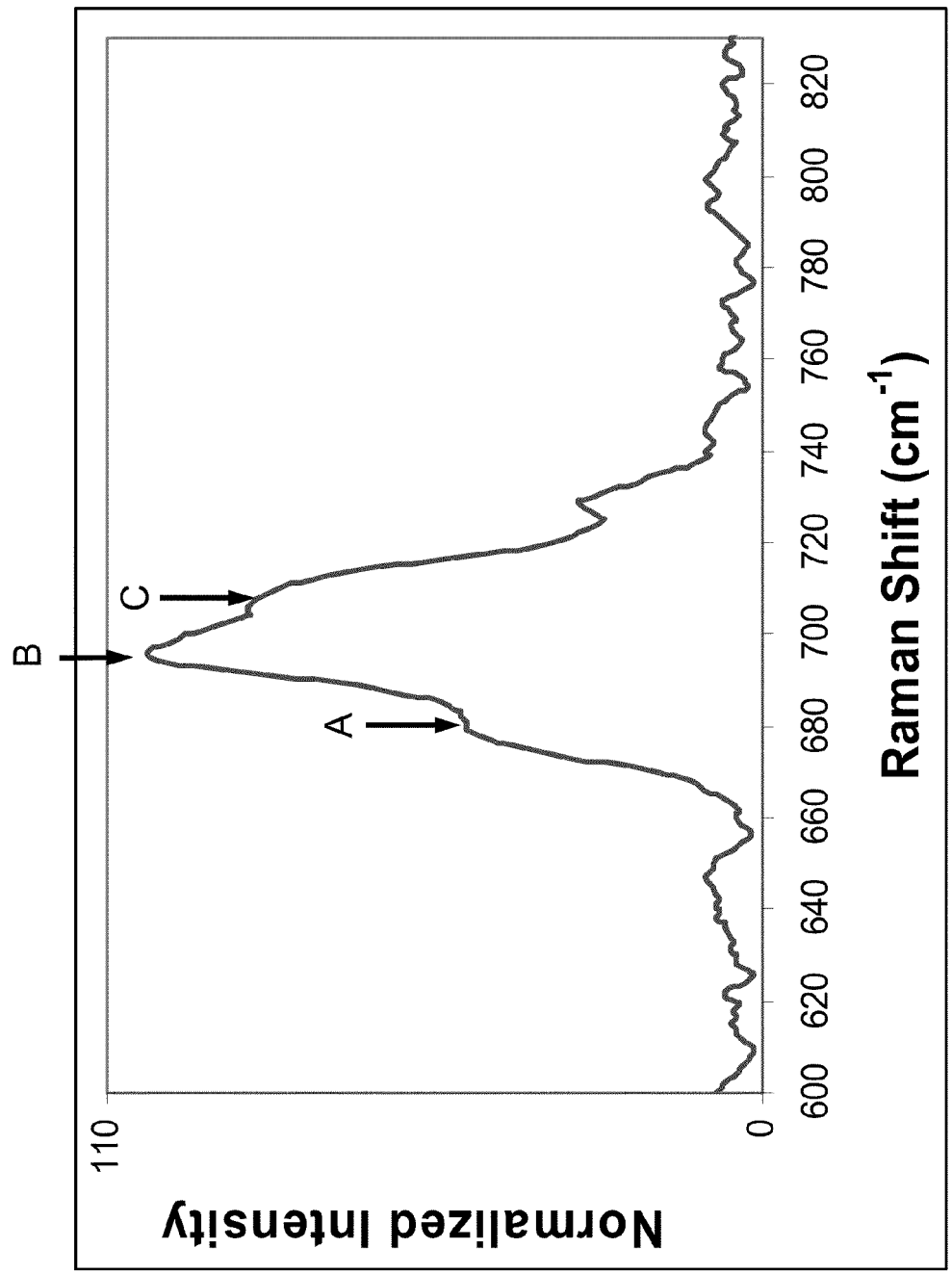

Raman spectra having spectral signatures for an illegal and harmful chemical (melamine) detected at different concentration levels in a milk product. FIG. 25A illustrates Raman spectra obtained from the milk sample solutions with melamine additive respectively at 0 ppm (no melamine additive), 1 ppm, 2 ppm, and 5 ppm concentration levels. FIG. 25B illustrates a Raman spectrum obtained from the milk sample solution having melamine additive at 50 ppm level. The Raman spectra shown in FIGS. 25A and 25B comprise Raman signature bands around 700 $cm^{-1}$, which are approximately at 678 $cm^{-1}$ (Band A), 698 $cm^{-1}$ (Band B), and 712 $cm^{-1}$ (Band C), respectively. Moreover, it was observed that Band A at about 678 $cm^{-1}$ increases in relative strength among the three bands as the melamine concentration is increased. In contrast, Band C at about 712 $cm^{-1}$ decreases in relative strength as melamine concentration increases. These two trends can be clearly seen by comparing the Raman spectra at the 5 ppm (FIG. 25A) and 50 ppm (FIG. 25B) melamine levels.

Figure 26:
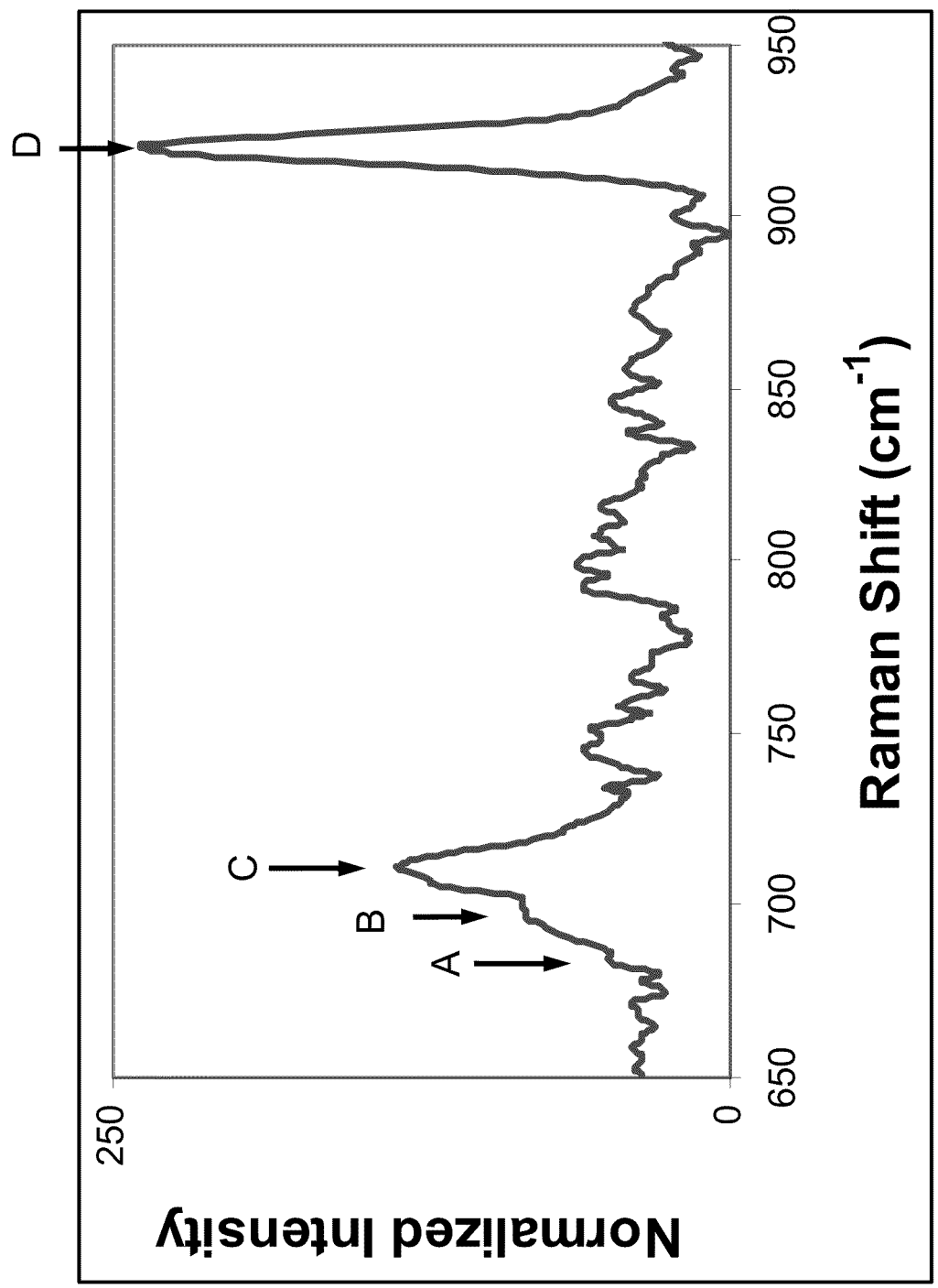
FIG. 26 illustrates a Raman spectrum having a spectral signature for melamine detected in a milk solution using 918 $cm^{-1}$ Raman band of the acetonitrile as an internal standard reference.

In another example, acetonitrile solvent can be added to a sample milk solution as an internal standard reference for the Raman scattering measurement. Acetonitrile is used as a solvent because it was found that the Raman scattering strength is not or weakly coupled to test solution. Referring to FIG. 26, a Raman spectrum is obtained, with the Raman spectral signature around 700 $cm^{-1}$ (Band A, B and C), from a milk solution having a melamine concentration at 5 ppm and with the addition of the acetonitrile using the above described system and methods. A Raman band (Band "D") is found at around 918 $cm^{-1}$-921 $cm^{-1}$, which can be used as an internal standard reference for calibrating Raman band frequency and intensity. Another Raman band exists at around 1640 $cm^{-1}$.

Figure 27:
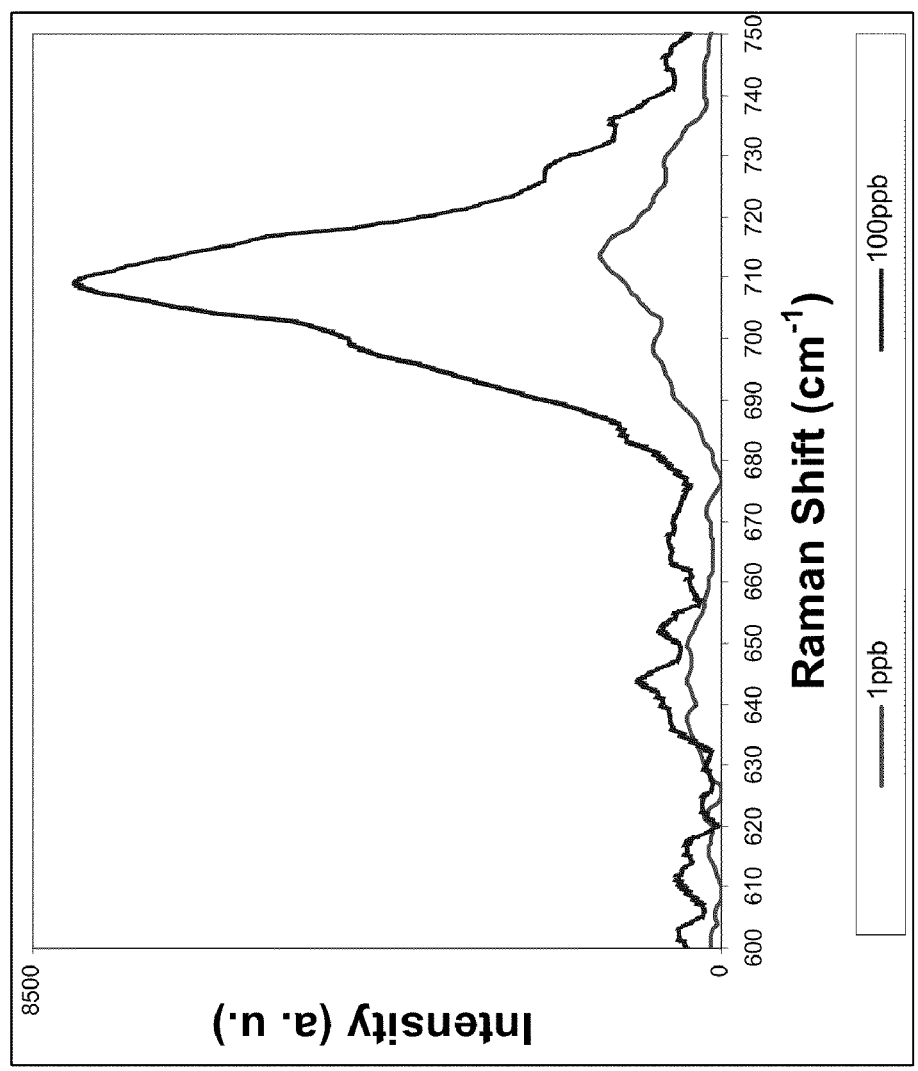
FIG. 27 illustrates Raman spectra having spectral signatures for an illegal and harmful chemical (melamine) detected at different concentration levels in water.

In another example, Raman spectra having spectral signatures for an illegal and harmful chemical (melamine) detected at different concentration levels, 1 ppb (parts per billion) and 100 ppb, in aqueous solution (FIG. 27).

In some embodiments, referring to FIGS. 1B, FIGS. 16F, 16E, and 16H, a metal film is coated on the nano rods 108 (or holes) on the nano surfaces of the sensor 105. The metallic film is electrically connected to an electrode. The metallic film can be formed by a noble metal such as gold. To apply a sample solution to the sensor surface, the sensor is submerged in the sample solution. An electric bias potential is applied to the electrode and the metallic film. The electrical bias potential can be controlled in the range from −3.0 to +3.0V, which can enhance the adsorption of the sample molecules (e.g., melamine molecules) to the nano surfaces, to enhance local electromagnetic filed, and enhance charge transfer between sample molecules and nano surface structures, which can enhance the intensity of Raman scattering from the sample molecules adsorbed on the nano surfaces. The incident laser beam can be projected on the sensor and the scattered light detected while the potential bias is being applied to the sample solution. The Raman light scattering measurement can also be conducted after the electrical bias potential is withdrawn.

In some embodiments, ion-exchange column is a means of separation of interferences from the samples. After sample passed the column, interferences retain on the column and analytes are flute out. The column, for example, $C_{18}$ column, also can be employed that can separate chemicals in different retention times that chemical properties are similar. The final purified sample would result in increasing the limit of detection up to 2-6 orders.

In some embodiments, the detection of chemicals in food or for disease diagnosis can be conducted using an integrated device that is capable of chemical separation and light scattering detection of trace chemicals, biological materials, etc. Details about such an integrated device are disclosed in commonly assigned U.S. patent application Ser. No. 11/761,453, entitled "Integrated Chemical Separation Light Scattering Device", filed Jun. 12, 2007, the disclosure is incorporated by reference herein.

Figure 28:
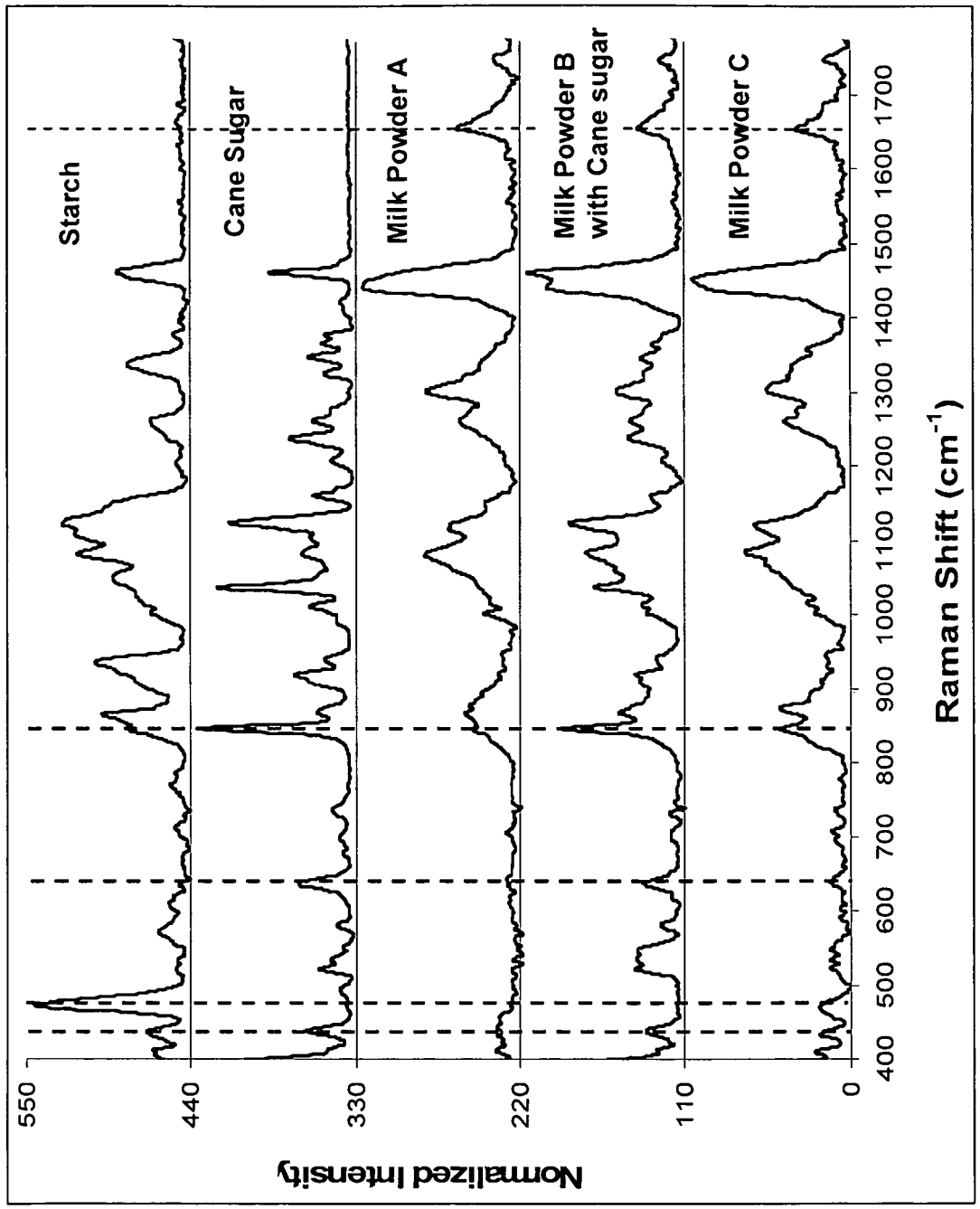
FIG. 28 illustrates Raman spectra for identifying unauthorized additive chemicals in a milk powder product.

In some embodiments, the disclosed light scattering probe and disclosed chemical detection methods can also be applied to detect useful or neutral ingredients as well as illegal or harmful ingredients in food products. FIG. 28 illustrates, from top to bottom, Raman spectra from starch, cane sugar, a milk powder A (a first milk powder brand), a milk powder B (a second milk powder brand) containing with cane sugar additive, and milk powder C (a third milk powder brand). Starch and cane sugars are not supposed to be in normal milk powders. But because starch and cane sugars are white powders, they are not easily detected with normal test methods when they are mixed in milk powder. The Raman spectrum (at the top of FIG. 28) shows a very strong band at around 473 $cm^{-1}$, which provides an evidence for starch content in a milk powder. This signature Raman band can be used to detect if starch is mixed into milk power. The detection method is applicable to the unauthorized mixing of starch containing materials such as flour, rice powder, soybean powder, potato powder, sweet potato powder, etc.

The disclosed systems and methods can also be used to screen the existence of cane sugar in milk powders. The Raman spectra (second from the top in FIG. 28) shows several strong Raman bands (around 850 $cm^{-1}$, 940 $cm^{-1}$, 1020 $cm^{-1}$, 1130 $cm^{-1}$ and so on). The collective characteristics of these Raman bands are visible in the spectrum obtained from milk powder B mixed with cane sugar (fourth from the top in FIG. 28), which is legal since the milk powder B package labeled related cane sugar mixing, but absent from the spectrum obtained from milk powder A without cane sugar additive (third from the top in FIG. 28). On the other hand, the collective characteristics of cane sugar related Raman bands are visible in the spectrum obtained from milk powder C (bottom spectrum of FIG. 28), which the milk powder is illegal sine its package label didn't show related cane sugar. Note that Raman test shows that milk powder C was mixed with both starch and cane sugar without package labeling.

Furthermore, the disclosed methods and systems can be applied to determine level of protein contained in a food product such as in a dairy product. A high concentration of protein in a food product can be reflected by high amide I concentration which carries Raman signature band at around 1658 cm$^{-1}$. The intensity at 1658 cm$^{-1}$ relative to other spectral features can be used to quantify the protein level in a food product such as a milk powder. For example, the three different samples of milk powders in FIG. 28 (shown in the lower three spectra in FIG. 28) are of similar protein levels. The more pronounced peak at 1658 cm$^{-1}$ for milk powder A shows milk powder A contains slightly higher protein level than milk powder B and milk powder C.

The disclosed methods and systems are therefore effective means for detecting protein levels, the existence of cane sugar, starch, and illegal additives such as melamine in milk powders. Moreover, the disclosed systems are compact and portable. The substance detection can be easily conducted on site with a fast turn around time (5 to 10 minutes or even shorter time), which can enable timely and effective authentication and quality verification of milk contained products, such as milk and powder in a wide range of circumstances.

Figure 29:
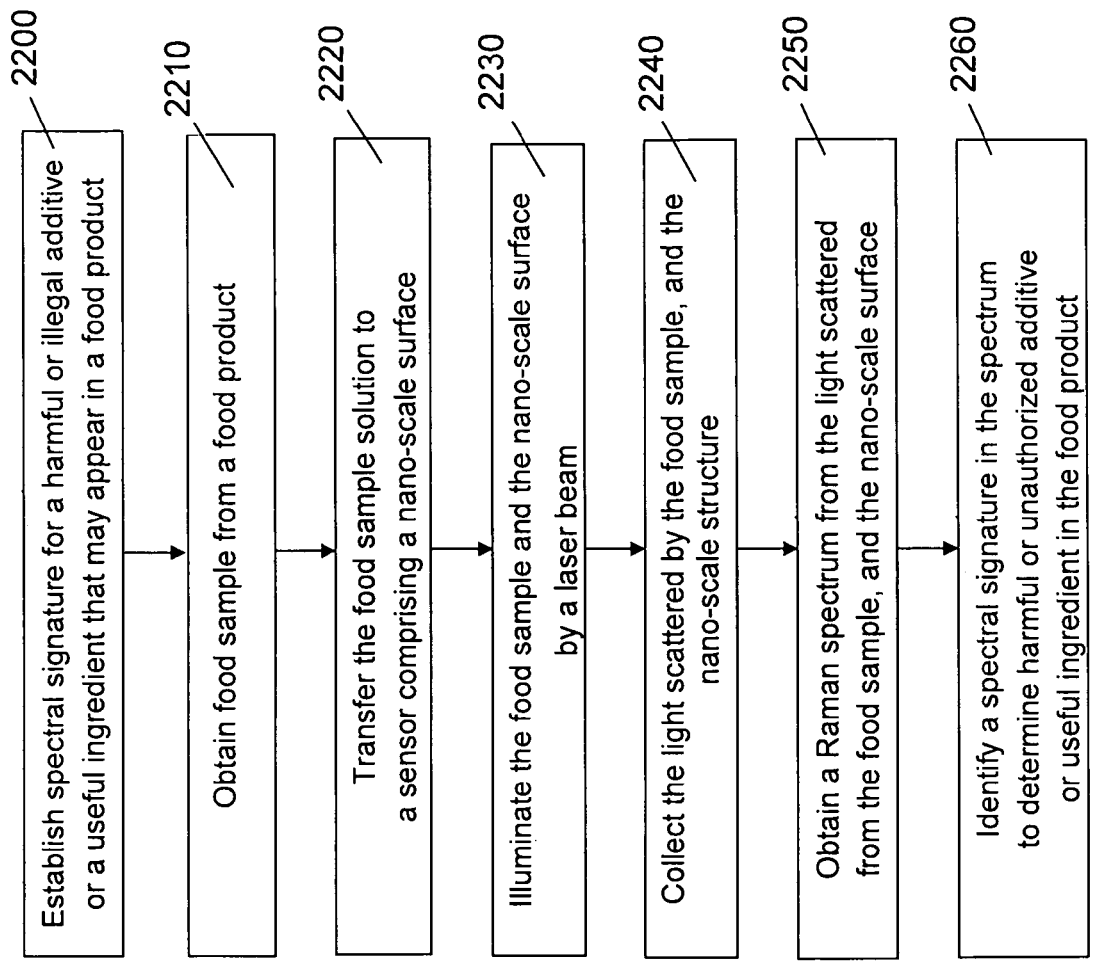
FIG. 29 is a flowchart for detecting harmful chemicals in food products for assuring food safety.

The detection of harmful chemicals in food products using the disclosed Raman scattering probe can include one of more of the following steps: referring to FIG. 29, spectral signatures for harmful or unauthorized, useful ingredients or protein (amide I) that may appear in a food product are first established (step 2200). This can be achieved by conducting Raman scattering measurement on a reference solution of a harmful or useful ingredient applied to nano surface structures on a light scattering sensor as described above. The wavelengths and spectral characteristics (peak height, peak width etc.) can be stored in a library in the spectral analyzer (150 in FIG. 6). A threshold value can also be determined for the peak height of the spectral signature, which can correspond to certain predetermined concentration of the chemical in the reference solution. In some embodiments, the signal-to-noise ratio of the spectral peak is calculated. The chemical can be positively identified, if the signal-to-noise ratio is above certain threshold (such as 3).

In some embodiments, the sensor used for establishing the spectral signature includes substantially the same nano structures as the sensors to be used for detecting or quantifying chemical substance in the food products. In other words, the dimensions and shape of the nano rods or nano holes, the spacing between the nano rods and nano holes, as well as the material compositions of the nano rods and nano holes are substantially the same for the sensor used for establishing the spectral signature and for in-field testing of food product. For instance, the same sensor model can be used for both purposes. This approach can assure the best matching of spectral characteristics between a measured spectrum and a spectral signature. The approach can also minimize noise that can be caused by structural differences between different sensor structures and material compositions.

In some embodiments, the nano surface structure used for establishing Raman spectral signature for a chemical can be prepared by a test solution that includes the target chemical and a suspension of nano particles. The original sensor surface can be relatively flat. The test solution is applied to the sensor surface. After evaporation, a layer of nano particles adsorbed with the target chemical's molecules are deposited on the sensor surface, which is subject to Raman scattering measurement for establishing the Raman signature. The same procedure can be followed in detection of an ingredient in a food product or a substance in a body fluid from a patient except that the target chemical is replaced by a sample solution of the food sample or the body fluid. To improve test sensitivity and reduce noise in the analysis, the same nano particles and the same solvent are preferably used for the Raman signature testing and the in-field substance detection. In other words, the size distribution and material composition of the nano particles used in establishing the Raman spectral signature and the in-field measurement can be substantially the same.

A food sample is first obtained from a food product (step 2210 in FIG. 29). Due to the high sensitivity of the disclosed Raman scattering sensors, the amount food sample solution can be rather small. For example, the volume of the food sample solution obtained from the field can be in a range from about 100 pl to 1 ml. Examples of the food sample can include dairy products, candies, drinks, alcohol, meat, water products (such as fish, shrimp, etc.), tea, fresh or canned vegetables, fruits, grain products, cereals, corn chips, or potato chips, etc. The food sample can be prepared or dissolved in a solution and transferred to a sensor comprising a nano-scale surface structure (step 2220). Molecules in the food sample solution are adsorbed to the nano-scale surface structure. A laser beam is applied to illuminate the food sample solution, the nano-scale surface structure, and the molecules adsorbed onto the nano-scale surface structure (step 2230). Light scattered by the food sample solution, the nano-scale surface structure, and the adsorbed molecules is collected (step 2240). The test can also be carried out with mixing test sample with test reagent containing noble metal (such as silver Ag, gold Au, etc.) nano particles with averaged particle diameter in the range of about 2 and about 100 nm, Then, light scattered by the mixed sample solution, with or without the nano-scale surface structure, and the adsorbed molecules is collected (step 2240).

A Raman spectrum is obtained from the scattered light (step 2250). One or more spectral signatures are identified in the spectrum to determine harmful or illegal additives and ingredients, or to verify the existence and concentration levels of useful ingredients (step 2260). Examples of the harmful or illegal additives or ingredients, common fertilizer chemicals, weed control chemicals, pesticides, insecticides, antibiotics, hormones, and preserving chemicals, such as melamine, sodium cyclamate (sodium cyclohexylsulfamate) cane sugar, starch, nitrite, nitrate, Sudan I, II, III and IV, malachite green, methomidophos, acephate, DDT, DDV, malathion, fenitrothion, deltamethrin, cypermethrin, methy parathion, phosmet, nitro furan (for example, furanzolidole), dimethoate, chloramphenicol, chlortetracycline, ciprofloxacin, clenbuterol, enorfloxacin, etc. Wavelengths and the characteristics of the relevant spectral signatures in Raman spectra are specific to each chemical to be detected or quantified, as described above in relation to FIGS. 25A-28. A spectral signature can include a spectral peak. The spectral signature can be identified when the spectral peak is above certain threshold, which can be predetermined by analyzing the reference solutions containing the chemical as described above. For example, a signal-to-noise ratio of the spectral peak relative to the noise background can be above 3 for the spectral signature to be positively identified.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention. For example, nano surface structures applicable to the disclosed systems and methods are not limited to the examples described. The nano surface structures can include nano rods (or columns), nano holes (or pores), and other nano surface textures, and a deposit of nano particles coated on a sensor surface.

What is claimed is:

1. A method for detecting an ingredient in a food product, comprising:
   establishing a spectral signature in a Raman spectrum obtained from a chemical substance;
   allowing a food sample solution obtained from a food product to come into contact with a first nano-scale surface structure in a first sensor;
   illuminating the food sample solution and the first nano-scale surface structure on the first sensor by a laser beam;
   scattering the laser beam by the food sample solution and the first nano-scale surface structure to produce a scattered light;
   obtaining a first Raman spectrum from the scattered light using a spectral analyzer; and
   identifying the spectral signature around a predetermined wavelength in the first Raman spectrum to determine the existence of the chemical substance in the food product,
   wherein the step of establishing comprises: allowing a reference sample solution containing the chemical substance to come to contact with a second nano-scale surface structure in a second sensor; and obtaining a second Raman spectrum from the reference solution and the nano surface to establish the spectral signature in the Raman spectrum for the chemical substance;
   wherein the spectral signature includes at least one spectral peak around the predetermined wavelength in the first Raman spectrum; and
   wherein the step of identifying comprises: determining if the spectral peak in the first Raman spectrum or a signal-to-noise ratio for the spectral peak is above a pre-determined threshold value; and positively identifying the chemical substance if the spectral peak or the signal-to-noise ratio is above the pre-determined threshold value.

2. The method of claim 1, wherein the first sensor and the second sensor have substantially the same nano surface structures.

3. The method of claim 1, wherein the sensor further comprises a conductive material on the substrate.

4. The method of claim 3, further comprising: during the step of illuminating, applying an electric potential to the conductive material in the first nano-scale surface structure to enhance charge transfer between molecules of the conductive material and the conductive material in the first nano-scale surface structure.

5. The method of claim 1, wherein the first sensor comprises a substrate, wherein the nano-scale surface structure comprises a plurality of columns over the substrate or a plurality of holes in the substrate.

6. The method of claim 5, wherein the plurality of columns or the plurality of holes have an average neighboring distance in a range from 10 nanometers to 1000 nanometers.

7. The method of claim 1, further comprising introducing nano particles on a surface of the first sensor, wherein the first nano-scale surface structure includes the nano particles on the surface of the first sensor.

8. The method of claim 7, further comprising:
   suspending the nano particles in the food sample solution; and
   introducing the food sample solution to the surface of the first sensor.

9. The method of claim 1, further comprising determining a concentration of the chemical substance using the spectral signature if the chemical substance is determined to exist in the food product.

10. The method of claim 1, wherein the food product includes dairy products, candies, drinks, alcohol, meat, seafood, tea, fresh or canned vegetables, fruits, grain products, cereals, corn chips, potato chips, or protein containing food.

11. The method of claim 10, wherein the dairy products comprise milk, milk powders, cheese, cheese-containing cakes, yogurts, ice creams, or milk containing candies.

12. The method of claim 1, wherein the chemical substance comprises melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, or enorfloxacin.

13. The method of claim 1, wherein the product comprises a dairy product, wherein the chemical substance includes melamine, wherein the spectral signature comprises one or more of spectral peaks at about 678 $cm^{-1}$, 698 $cm^{-1}$, or 712 $cm^{-1}$, or at about 1648 $cm^{-1}$.

14. The method of claim 1, wherein the chemical substance includes protein, wherein the spectral signature comprises one or more of spectral peaks at about 1658 $cm^{-1}$.

15. The method of claim 1, wherein the chemical substance includes starch, wherein the spectral signature comprises one or more of spectral peaks at about 473 $cm^{-1}$.

16. A method for detecting an ingredient in a food product, comprising:
   allowing a reference sample solution containing the chemical substance to come into contact with a first nano-scale surface structure in a first sensor;
   obtaining a first Raman spectrum from the reference solution and the nano surface to establish a spectral signature in the first Raman spectrum for the chemical substance;
   allowing a food sample solution obtained from a food product to come to contact with a second nano-scale surface structure in a second sensor;
   illuminating the food sample solution and the second nano-scale surface structure on the second sensor by a laser beam;
   scattering the laser beam by the food sample solution and the second nano-scale surface structure to produce a scattered light;
   obtaining a second Raman spectrum from the scattered light using a spectral analyzer; and
   identifying the spectral signature around a predetermined wavelength in the second Raman spectrum to determine the existence of the chemical substance in the food product;
   wherein the spectral signature includes at least one spectral peak around the predetermined wavelength in the first Raman spectrum;
   wherein the step of identifying comprises: determining if the spectral peak in the second Raman spectrum or a signal-to-noise ratio for the spectral peak is above a pre-determined threshold value; and positively identifying the chemical substance if the spectral peak or the signal-to-noise ratio is above the pre-determined threshold value.

17. The method of claim 16, wherein the first sensor and the second sensor have substantially the same nano surface structures.

18. The method of claim 16, further comprising determining a concentration of the chemical substance using the spectral signature if the chemical substance is determined to exist in the food product.

19. The method of claim 16, wherein the food product includes dairy products, candies, drinks, alcohol, meat, seafood, tea, fresh or canned vegetables, fruits, grain products, cereals, corn chips, potato chips, or protein containing food.

20. The method of claim 16, wherein the chemical substance comprises melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, or enorfloxacin.

21. The method of claim 16, wherein the product comprises a dairy product, wherein the chemical substance includes melamine, wherein the spectral signature comprises one or more of spectral peaks at about 678 $cm^{-1}$, 698 $cm^{-1}$, or 712 $cm^{-1}$, or at about 1648 $cm^{-1}$.

22. The method of claim 16, wherein the chemical substance includes protein, wherein the spectral signature comprises one or more of spectral peaks at about 1648 $cm^{-1}$.

23. The method of claim 16, wherein the chemical substance includes starch, wherein the spectral signature comprises one or more of spectral peaks at about 473 $cm^{-1}$.

24. The method of claim 16, wherein the first nano-scale surface structure in a first sensor includes a plurality of columns or a plurality of holes having an average neighboring distance in a range from 10 nanometers to 1000 nanometers.

25. The method of claim 16, further comprising:
  introducing a first group of nano particles on a surface of the first sensor, wherein the first nano-scale surface structure includes the first group of nano particles on the surface of the first sensor; and
  introducing a second group of nano particles on a surface of the second sensor, wherein the second nano-scale surface structure includes the second group of nano particles on the surface of the second sensor.

26. The method of claim 25, wherein the first group of nano particles and the second group of nano particles have substantially the same size distribution and material composition.

27. The method of claim 25, further comprising:
  suspending the second group of nano particles in the food sample solution; and
  introducing the food sample solution to the surface of the second sensor.

28. A method for detecting an ingredient in a food product, comprising:
  allowing a reference sample solution containing a chemical substance to come into contact with a first nano-scale surface structure in a first sensor, wherein the first nano-scale surface structure includes a plurality of nano particles on a surface of the first sensor, or a plurality of columns or holes having an average neighboring distance in a range from 10 nanometers to 1000 nanometers;
  obtaining a first Raman spectrum from the reference solution and the nano surface to establish a spectral signature around a predetermined wavelength in the first Raman spectrum for the chemical substance, wherein the spectral signature includes at least one spectral peak around the predetermined wavelength in the first Raman spectrum;
  allowing a food sample solution obtained from a food product to come into contact with a second nano-scale surface structure in a second sensor, wherein the first sensor and the second sensor have substantially the same nano surface structures;
  illuminating the food sample solution and the second nano-scale surface structure on the second sensor by a laser beam;
  scattering the laser beam by the food sample solution and the second nano-scale surface structure to produce a scattered light;
  obtaining a second Raman spectrum from the scattered light using a spectral analyzer;
  identifying the spectral signature around the predetermined wavelength in the second Raman spectrum to determine the existence of the chemical substance in the food product, wherein the step of identifying comprises determining if the spectral peak in the second Raman spectrum or a signal-to-noise ratio for the spectral peak in the second Raman spectrum is above a pre-determined threshold value; and
  positively identifying the chemical substance if the spectral peak or the signal-to-noise ratio is above the pre-determined threshold value.

29. The method of claim 28, wherein the product comprises a dairy product, wherein the chemical substance includes melamine, wherein the spectral signature comprises one or more of spectral peaks at about 678 $cm^{-1}$, 698 $cm^{-1}$, or 712 $cm^{-1}$, or at about 1648 $cm^{-1}$.

30. The method of claim 28, wherein the chemical substance includes protein, wherein the spectral signature comprises one or more of spectral peaks at about 1648 $cm^{-1}$.

* * * * *